US008715955B2

(12) United States Patent
Donovan et al.

(10) Patent No.: US 8,715,955 B2
(45) Date of Patent: May 6, 2014

(54) LASER MICRODISSECTION APPARATUS AND METHOD

(75) Inventors: Brian W. Donovan, San Jose, CA (US); Thomas M. Baer, Mountain View, CA (US)

(73) Assignee: Life Technologies Corporation, Carlsbad ( * ) Notice: Subject to any disclaimer, the term of this patent is extended or adjusted under 35 U.S.C. 154(b) by 1742 days.

(21) Appl. No.: 11/222,281

(22) Filed: Sep. 8, 2005

(65) Prior Publication Data

US 2006/0087643 A1    Apr. 27, 2006

Related U.S. Application Data

(60) Provisional application No. 60/608,351, filed on Sep. 9, 2004, provisional application No. 60/608,352, filed on Sep. 9, 2004, provisional application No. 60/608,353, filed on Sep. 9, 2004.

(51) Int. Cl.
*G01N 1/28*    (2006.01)
(52) U.S. Cl.
USPC ......... 435/40.5; 435/40.52; 435/378; 356/36; 156/60; 156/251; 156/272.8; 250/492.1
(58) Field of Classification Search
USPC .......................................................... 356/36
See application file for complete search history.

(56) References Cited

U.S. PATENT DOCUMENTS

| | | |
|---|---|---|
| 3,680,947 A | 8/1972 | Wanesky |
| 3,705,769 A | 12/1972 | Johannsmeier |
| 3,848,962 A | 11/1974 | Nelson |
| 4,210,384 A | 7/1980 | Meyer et al. |
| 4,303,866 A | 12/1981 | Porro et al. |
| 4,333,983 A | 6/1982 | Allen |
| 4,436,385 A | 3/1984 | Fischer et al. |
| 4,508,435 A | 4/1985 | Graham et al. |
| 4,509,834 A | 4/1985 | Hodgson |
| 4,538,885 A | 9/1985 | Graham et al. |
| 4,552,033 A | 11/1985 | Märzhäuser |
| 4,600,282 A | 7/1986 | Yamamura et al. |
| 4,614,431 A | 9/1986 | Komeyama |
| 4,623,839 A | 11/1986 | Garretson et al. |
| 4,627,009 A | 12/1986 | Holmes et al. |
| 4,672,559 A | 6/1987 | Jansson et al. |
| 4,673,261 A | 6/1987 | Hunt et al. |
| 4,684,781 A | 8/1987 | Frish et al. |
| 4,702,565 A | 10/1987 | Schilling et al. |
| 4,731,530 A | 3/1988 | Mikan |
| 4,760,385 A | 7/1988 | Jansson et al. |
| 4,807,984 A | 2/1989 | Kurimura et al. |
| 4,824,229 A | 4/1989 | Narita et al. |
| 4,836,667 A | 6/1989 | Ozeki |
| 4,852,985 A | 8/1989 | Fujihara et al. |
| 4,856,873 A | 8/1989 | Kleinberg |
| 4,871,245 A | 10/1989 | Ishikawa et al. |
| 4,920,053 A | 4/1990 | Inoue et al. |
| 4,923,294 A | 5/1990 | Courtenay |
| 4,954,715 A | 9/1990 | Zöld |
| 4,964,708 A | 10/1990 | Mason |
| 4,987,006 A | 1/1991 | Williams et al. |
| 4,992,660 A | 2/1991 | Kobayashi |
| 5,017,428 A | 5/1991 | Mecke et al. |
| 5,029,791 A | 7/1991 | Ceccon et al. |
| 5,037,207 A | 8/1991 | Tomei et al. |
| 5,057,689 A | 10/1991 | Nomura et al. |
| 5,077,620 A | 12/1991 | Mauro |

(Continued)

FOREIGN PATENT DOCUMENTS

| | | |
|---|---|---|
| CH | 566 015 | 8/1975 |
| DE | 1 263 339 | 3/1968 |

(Continued)

OTHER PUBLICATIONS

U.S. Appl. No. 60/163,634, filed Nov. 4, 1999, Baer et al.
U.S. Appl. No. 60/245,884, filed Nov. 6, 2000, Baer et al.
U.S. Appl. No. 09/018,452, filed Feb. 4, 1998, Baer et al.
U.S. Appl. No. 09/121,677, filed Jul. 23, 1998, Baer et al.
U.S. Appl. No. 09/121,691, filed Jul. 23, 1998, Baer et al.
U.S. Appl. No. 09/617,742, filed Jul. 17, 2000, Baer et al.
U.S. Appl. No. 09/706,332, filed Nov. 6, 2000, Baer et al.
Allred, D. Craig and Mohsin, Syed K. "Biological features of human premalignant breast disease," in Harris, J: R. *Disease of the Breast* (Philadelphia, Lippicott Williams & Wilkins, 2000), pp. 355-366.
Anonymous "ChromaVision" website product description including Rare Cell Detection in Tissue and Rare Cell Detection in Cytospin Prep—retrieval date Jun. 21, 2004.

(Continued)

*Primary Examiner* — Allison Ford
*Assistant Examiner* — Susan E Fernandez

(57) ABSTRACT

Systems and methods for automated laser microdissection are disclosed. In one variation, targeted biological material is manually or automatically selected and a transfer film is placed in juxtaposition to the location of an interior of a cut path. In another variation, a sample of biological material is mounted onto a polymer membrane which is then placed onto a substrate. Targeted biological material is manually or automatically selected and a transfer film is placed in juxtaposition with the targeted biological material on the side of the biological material. In yet another variation, a sample of biological material is mounted onto a polymer membrane which is then inverted onto a substrate. Targeted biological material is manually or automatically selected and a transfer film is placed in juxtaposition with the targeted biological material on the side of the polymer membrane. Then, an UV laser cuts along a cut path around the targeted portions of biological material in a closed cut path or a substantially closed cut path defining an interior and an exterior portion of the tissue sample. In a substantially closed cut path, bridges are left spanning the interior of the cut path and the exterior of the cut path. An IR laser activates at least a portion of the transfer film such that the transfer film in the vicinity of targeted portion adheres to the biological material interior to the cut path. The transfer film is then removed separating the targeted portions of biological material which are adhered to the transfer film from the remaining portion of the tissue sample.

10 Claims, 22 Drawing Sheets

(56) References Cited

U.S. PATENT DOCUMENTS

| | | |
|---|---|---|
| 5,089,909 A | 2/1992 | Kleinberg |
| 5,103,338 A | 4/1992 | Crowley et al. |
| 5,126,877 A | 6/1992 | Biber |
| 5,143,552 A | 9/1992 | Moriyama |
| 5,162,941 A | 11/1992 | Favro et al. |
| 5,165,297 A | 11/1992 | Krueger |
| 5,173,802 A | 12/1992 | Heller |
| 5,173,803 A | 12/1992 | Heller |
| 5,225,326 A | 7/1993 | Bresser et al. |
| 5,253,110 A | 10/1993 | Ichihara et al. |
| 5,257,182 A | 10/1993 | Luck et al. |
| 5,262,891 A | 11/1993 | Nakasato |
| 5,263,384 A | 11/1993 | Suzuki |
| 5,280,384 A | 1/1994 | Shibasaki |
| 5,287,272 A | 2/1994 | Rutenberg et al. |
| 5,288,996 A | 2/1994 | Betzig et al. |
| 5,296,963 A | 3/1994 | Murakami et al. |
| 5,298,963 A | 3/1994 | Moriya et al. |
| 5,312,393 A | 5/1994 | Mastel |
| 5,323,009 A | 6/1994 | Harris |
| 5,337,178 A | 8/1994 | Kung et al. |
| 5,345,333 A | 9/1994 | Greenberg |
| 5,357,366 A | 10/1994 | Marchlenski |
| 5,359,417 A | 10/1994 | Müller et al. |
| 5,367,401 A | 11/1994 | Saulietis |
| 5,378,675 A | 1/1995 | Takeyama et al. |
| 5,386,112 A | 1/1995 | Dixon |
| 5,393,647 A | 2/1995 | Neukermans et al. |
| 5,403,735 A | 4/1995 | Maruhashi et al. |
| 5,403,970 A | 4/1995 | Aoki |
| 5,412,503 A | 5/1995 | Nederlof |
| 5,420,716 A | 5/1995 | Fukaya |
| 5,434,703 A | 7/1995 | Morizumi |
| 5,450,233 A | 9/1995 | Yamamoto et al. |
| 5,455,420 A | 10/1995 | Ho et al. |
| 5,465,375 A | 11/1995 | Thepaut et al. |
| 5,468,967 A | 11/1995 | Chan et al. |
| 5,471,260 A | 11/1995 | Luce et al. |
| 5,479,252 A | 12/1995 | Worster et al. |
| 5,487,117 A | 1/1996 | Burges et al. |
| 5,492,861 A | 2/1996 | Opower |
| 5,497,430 A | 3/1996 | Sadovnik et al. |
| 5,504,366 A | 4/1996 | Weiss et al. |
| 5,506,725 A | 4/1996 | Koike et al. |
| 5,510,615 A | 4/1996 | Ho et al. |
| 5,517,353 A | 5/1996 | Ikoh et al. |
| 5,532,128 A | 7/1996 | Eggers et al. |
| 5,532,476 A | 7/1996 | Mikan |
| 5,532,873 A | 7/1996 | Dixon |
| 5,535,052 A | 7/1996 | Jörgens |
| 5,536,941 A | 7/1996 | Swann |
| 5,537,863 A | 7/1996 | Fujiu et al. |
| 5,552,928 A | 9/1996 | Furuhashi et al. |
| 5,556,790 A | 9/1996 | Pettit |
| 5,557,456 A | 9/1996 | Garner et al. |
| 5,558,329 A | 9/1996 | Liu |
| 5,559,329 A | 9/1996 | Joseph et al. |
| 5,578,832 A | 11/1996 | Trulson et al. |
| 5,587,748 A | 12/1996 | Luce et al. |
| 5,587,833 A | 12/1996 | Kamentsky |
| 5,598,888 A | 2/1997 | Sullivan et al. |
| 5,602,674 A | 2/1997 | Weissman et al. |
| 5,619,035 A | 4/1997 | Weiss et al. |
| 5,621,207 A | 4/1997 | O'Mara |
| 5,625,705 A | 4/1997 | Recht |
| 5,631,734 A | 5/1997 | Stern et al. |
| 5,638,206 A | 6/1997 | Sumiya et al. |
| 5,659,421 A | 8/1997 | Rahmel et al. |
| 5,707,801 A | 1/1998 | Bresser et al. |
| 5,715,327 A | 2/1998 | Wilhelm et al. |
| 5,728,527 A | 3/1998 | Singer et al. |
| 5,734,735 A | 3/1998 | Coleman, Jr. |
| 5,740,269 A | 4/1998 | Oh et al. |
| 5,740,270 A | 4/1998 | Rutenberg et al. |
| 5,745,601 A | 4/1998 | Lee et al. |
| 5,751,839 A | 5/1998 | Drocourt et al. |
| 5,767,923 A | 6/1998 | Coleman, Jr. |
| 5,774,357 A | 6/1998 | Hoffberg et al. |
| 5,778,108 A | 7/1998 | Coleman, Jr. |
| 5,787,188 A | 7/1998 | Nelson et al. |
| 5,843,644 A | 12/1998 | Liotta et al. |
| 5,843,657 A | 12/1998 | Liotta et al. |
| 5,859,699 A | 1/1999 | Baer et al. |
| 5,867,690 A | 2/1999 | Lee |
| 5,870,493 A | 2/1999 | Vogl et al. |
| 5,875,108 A | 2/1999 | Hoffberg et al. |
| 5,889,880 A | 3/1999 | Doerrer et al. |
| 5,920,360 A | 7/1999 | Coleman, Jr. |
| 5,920,477 A | 7/1999 | Hoffberg et al. |
| 5,939,278 A | 8/1999 | Boon et al. |
| 5,959,697 A | 9/1999 | Coleman, Jr. |
| 5,978,497 A | 11/1999 | Lee et al. |
| 5,985,085 A | 11/1999 | Baer et al. |
| 5,987,158 A | 11/1999 | Meyer et al. |
| 5,998,129 A * | 12/1999 | Schutze et al. .................. 435/4 |
| 5,999,634 A | 12/1999 | Abbott et al. |
| 6,010,888 A | 1/2000 | Liotta et al. |
| 6,031,232 A | 2/2000 | Cohenford et al. |
| 6,061,471 A | 5/2000 | Coleman, Jr. |
| 6,100,051 A | 8/2000 | Goldstein et al. |
| 6,133,943 A | 10/2000 | Needham |
| 6,134,354 A | 10/2000 | Lee et al. |
| 6,143,535 A | 11/2000 | Palsson |
| 6,146,897 A | 11/2000 | Cohenford et al. |
| 6,148,099 A | 11/2000 | Lee et al. |
| 6,157,446 A | 12/2000 | Baer et al. |
| 6,181,811 B1 | 1/2001 | Kuan et al. |
| 6,184,973 B1 | 2/2001 | Baer et al. |
| 6,204,030 B1 | 3/2001 | Liotta et al. |
| 6,215,550 B1 | 4/2001 | Baer et al. |
| 6,215,892 B1 | 4/2001 | Douglass et al. |
| 6,226,392 B1 | 5/2001 | Bacus et al. |
| 6,229,568 B1 | 5/2001 | Kawaguchi et al. |
| 6,240,209 B1 | 5/2001 | Wilcke |
| 6,259,807 B1 | 7/2001 | Ravkin |
| 6,327,377 B1 | 12/2001 | Rutenberg et al. |
| 6,337,926 B2 | 1/2002 | Takahashi et al. |
| 6,469,779 B2 | 10/2002 | Baer et al. |
| 6,495,195 B2 | 12/2002 | Baer et al. |
| 6,512,576 B1 | 1/2003 | Baer et al. |
| 6,528,248 B2 | 3/2003 | Lossing et al. |
| 6,531,318 B1 | 3/2003 | Palmer-Toy et al. |
| 6,569,639 B2 | 5/2003 | Liotta et al. |
| 6,690,470 B1 | 2/2004 | Baer et al. |
| 6,697,149 B2 | 2/2004 | Baer et al. |
| 7,027,133 B2 | 4/2006 | Baer et al. |
| 7,075,640 B2 | 7/2006 | Baer et al. |
| 2002/0001837 A1 | 1/2002 | Baer et al. |
| 2002/0090122 A1 | 7/2002 | Baer et al. |
| 2002/0142412 A1 | 10/2002 | Ogawa et al. |
| 2003/0032082 A1* | 2/2003 | Leclerc .................. 435/40.5 |
| 2003/0058430 A1* | 3/2003 | Baer et al. .................. 356/36 |
| 2004/0063326 A1 | 4/2004 | Szlufcik et al. |
| 2004/0093166 A1 | 5/2004 | Kil |
| 2006/0023201 A1* | 2/2006 | Malekafzali .................. 356/36 |
| 2006/0087643 A1 | 4/2006 | Donovan et al. |

FOREIGN PATENT DOCUMENTS

| | | |
|---|---|---|
| DE | 196 03 996 | 8/1997 |
| DE | 196 36 074 | 3/1998 |
| EP | 0 748 439 | 7/1999 |
| WO | WO 91/07683 | 5/1991 |
| WO | WO 94/02646 | 2/1994 |
| WO | WO 95/23960 | 9/1995 |
| WO | WO 95/30919 | 11/1995 |
| WO | WO 97/13838 | 4/1997 |
| WO | WO 98/35216 | 8/1998 |
| WO | WO 98/44446 | 10/1998 |
| WO | WO 01/33190 | 5/2001 |
| WO | WO 02/37159 | 5/2002 |
| WO | WO 02/057746 | 7/2002 |
| WO | WO 2004/025569 | 3/2004 |

(56) References Cited

FOREIGN PATENT DOCUMENTS

OTHER PUBLICATIONS

Ashkin, A. and Dziedzic, J.M. "Internal cell manipulation using infrared laser traps," *Proc. Nat. Acad. Sci*, 86:7914-7918 (1989).

Bonner, Robert F. et al. "Laser capture microdissection: Molecular analysis of tissue," *Science*, 278:1481-1483 (1997).

Duke University, "Evaluation of Cervical Cytology," AHCPR publication No. 99-E010 (Feb. 1999).

Emmert-Buck, M.R. et al. "Laser Capture Microdissection," *Science*, 274:998-1001 (1996).

Friend, T. "Getting up close to cancer genes," printed in *USA Today*, Science section, p. 4D, Aug. 5, 1977.

Frosini, G. et al. "A modified fuzzy C-means algorithm for feature selection," Peachfuzz 2000, 19th International Conference of the North American Fuzzy Information Processing Society (Piscataway, New Jersey) pp. 148-152 (2000) ISBN: 0-7803-6274-8.

Fukui, K. et al. "Microdissection of plant chromosomes by argon-ion laser beam," *Theoretical & Applied Genetics*, 84:787-791 (1992).

Goldstein, Seth R. et al. "Thermal modeling of laser capture microdissection," *Applied Optics*, 37(31):7378-7391 (1998).

Grohs, H. K. and Husain, O.A.N., eds. "Automated Cervical Cancer Screening," Igaku-Shoin Medical Publishers, Chapter 23, pp. 305-317 (1994).

Harlow, E. and Lane, D., eds. *Antibodies: A Laboratory Manual*. (New York, Cold Spring Harbor, 1988), pp. iii-ix (Table of Contents).

Heng, H. H. Q. et al. "High-Resolution Mapping of Mammalian Genes by In-Situ Hybridization to Free Chromatin," *Proc. Natl. Acad. Sci. USA*, 89:9509-9513 (1992).

Isenberg, G. et al. "Cell surgery by laser micro-dissection: a preparative method," *J. Microsc.*, 107(Pt 1):19-24 (1976).

Jarkrans, T. "Algorithms for Cell Image Analysis in Cytology and Pathology," *Comprehensive Summaries of Uppsala Dissertations* (1996).

Jeyendran, R. S. "Association of the in-vitro fertilizing capacity of human spermatozoa with sperm morphology as assessed by three classification systems," *Human Reprod.*, 1(5):305-308 (Aug. 1986).

Jiménez, C. R. et al. "Neuropeptide expression and processing as revealed by direct matrix-assisted laser desorption ionization mass spectrometry of single neurons," *Journal of Neurochemistry*, 62(1):404-407 (1994).

Jong-Min Park et al. "Analysis of active feature selection in optic nerve data using labeled fuzzy-C-means clustering," 2002 IEEE World Congress on Computational Intelligence. 2002 IEEE International Conference on Fuzzy Systems (Piscataway, New Jersey) 2:1580-1585 2002). ISBN: 0-7803-7280-8.

Koperski, K. et al. "Interactive models for semantic labeling of satellite images,"*EarthObserving Systems VII, Proceedings of the SPIE*, 4814:423-434 (Sep. 2002).

Kubo, Y. et al. "Early detection of Knudson's two-hits in preneoplastic renal cells of the Eker rat model by the laser microdissection procedure," *Cancer Research*, 55(5):989-990 (1995).

Kuska, Bob "New aim-and-shoot technique speeds up cell analysis," *J. Natl. Cancer Inst.*, 88(23):1708-1709 (1996).

Lawrence, J.B. et al. "Sensitive High-Resolution Chromatin and Chromosome Mapping In-Situ: Presence and Orientation of Two Closely Integrated Copies of EBV in a Lymphoma Line," *Cell*, 52:51-61 (1988).

Lewis, Ricki "Laser aids Alzheimer's study," *Biophotonics International* (Nov./Dec. 1998).

Lichter, P. et al. "High-Resolution Mapping of Human Chromosome 11 by In-Situ Hybridization with Cosmid Clones," *Science*, 247:64-69 (1990).

Manuelidis, L. et al. "High-Resolution Mapping of Satellite DNA Using Biotin-Labeled DNA Probes," *J. Cell. Biol.*, 95:619-625 (1982).

Morruzzi, J. F. et al. "Quantification and classification of human sperm morphology by computer assisted image analysis," *Fertil. Steril.*, 50(1):142-152 (Jul. 1988).

Meier-Ruge, W. et al. "The laser in the Lowry technique for microdissection of freeze-dried tissue slices," *Histochemical Journal*, 8:387-401 (1976).

Perez-Sanchez, F. "Morphometric Analysis of human sperm morphology," *Int. J. Androl.*, 17(5):248-255 (Oct. 1994).

Pizzi, A. "Diagnostic Cytology Learning Page," http://www-ocs. colorado.edu/-metzj/pizzia/learning_page.html Written Feb. 4, 1997, Last updated Aug. 4, 1998.

Salomie, A. et al. "Multivariate Techniques for Medical Image Segmentation," http://www.etro.vub.ac.be/members/deklerck.rudi/redimedia/segmentation/segment.htm.

Schachter, B. J. et al. "Some Experiments in Image Segmentation by Clustering of Local Feature Values," *Pattern Recognition*, (New York, Pergamon Press Inc., 1979).

Schindler, Melvin et al. "Automated analysis & survival selection of anchorage-dependent cells under normal growth conditions," *Cytometry*, 6(4):368-374 (1985).

Schindler, M. et al. "Select, microdissect & eject," *Nature Biotechnology*, 16(8):719-720 (1998).

Schültze, K. and Lahr, G. "Identification of expressed genes by laser-mediated manipulation of single cells," *Nature Biotechnology*, 16:737-742 (1998).

Simone, Nicole L. et al. "Laser capture microdissection: Opening the microscopic frontier to molecular analysis," *Trends Genet.*, 14(7):272-276 (1998).

Van den Engh, G. et al. "Estimating Genomic Distance from DNA Sequence Location in Cell Nuclei by a Random Walk Model," *Science*, 257:1410-1412 (1992).

Veigel, Claudia et al. "New cell biological applications of the laser microbeam technique: the microdissection and skinning of muscle fibers and the perforation and fusion of sarcolemma vesicles," *European Journal of Cell Biology*, 63(1):140-148 (1994).

Srinivasan, R., "Ablation of polymers and biological tissue by ultraviolet lasers," Science 234:559-565 (1986).

Office Action, in U.S. Appl. No. 11/236,045, mailed Feb. 27, 2009 (11 pages).

Reply to Office Action, in U.S. Appl. No. 11/236,045, filed May 27, 2009 (16 pages).

Office Action, in U.S. Appl. No. 11/236,045, mailed Aug. 20, 2009 (12 pages).

U.S. Appl. No. 60/613,038, filed Sep. 25, 2004, Baer et al.

U.S. Appl. No. 60/644,438, filed Mar. 23, 2005, Youngquist.

Reply to Office Action, in U.S. Appl. No. 11/236,045, filed Dec. 21, 2009 (16 pages).

* cited by examiner

LASER MICRODISSECTION APPARATUS AND METHOD

CROSS-REFERENCE TO RELATED APPLICATIONS

This application claims priority to U.S. Provisional Application Ser. No. 60/608,353, entitled "Laser microdissection apparatus and method," filed on Sep. 9, 2004; U.S. Provisional Application Ser. No. 60/608,351, entitled "Method and apparatus for laser microdissection with polymer film," filed on Sep. 9, 2004; and U.S. Provisional Application Ser. No. 60/608,352, entitled "Method and apparatus for laser microdissection with inverted polymer film," filed on Sep. 9, 2004; all of which are incorporated herein by reference in their entirety.

FIELD OF THE INVENTION

The invention relates generally to the field of laser microdissection. More particularly, the invention relates to microdissecting targeted regions of biological material from a tissue sample.

BACKGROUND

Tissue biopsies are frequently obtained for diagnostic and therapeutic purposes. Typically a tissue biopsy sample consists of a 5 to 10 micron slice of tissue that is placed on a glass microscope slide using techniques well known in the field of pathology. The tissue sample will typically consist of a variety of different types of cells. Often a pathologist will desire to remove only a small portion of the tissue for further analysis. Before the advent of laser microdissection, pathologists would have to resort to various time-consuming and imprecise microdissection techniques to obtain a sample of the desired region of a biopsy. Laser microdissection provides a simple method for the procurement of selected human cells from a heterogeneous population contained on a typical histopathology biopsy slide. The laser microdissection technique is generally described in the published article: Laser Capture Microdissection, Science, Volume 274, Number 5289, Issue 8, pp 998-1001, published in 1996, incorporated herein by reference, and in the following U.S. Pat. Nos. 5,859,699; 5,985,085; 6,184,973; 6,157,446; 6,215,550; 6,459,779; 6,495,195; 6,512,576; 6,528,248 all herein incorporated by reference in their entirety.

Laser microdissection systems generally comprise an inverted microscope fitted with a laser. Tissue samples are mounted, typically on a standard glass slide, and a transparent thermoplastic transfer film is placed over the dry section. This film is often manufactured containing organic dyes that are chosen to selectively absorb in the near infrared region of the spectrum overlapping the emission region of common AlGaAs laser diodes. When the film is exposed to the focused laser beam the exposed region is heated by the laser and melts, adhering to the tissue in the region that was exposed.

The laser melts the film in precise locations which serves to bind the film to a targeted cell or cells. Individual cells or clusters of cells can be targeted by the laser, depending on the diameter of light emitted from the laser. Heat generated by the laser is dissipated by the film, thus limiting the damage done to the targeted cells and the components therein. After the targeted cells are bound to the film, they are removed from the sample. The targeted cells are then extracted for further analysis. The transfer film can be mounted on a transparent cap that fits on a microcentrifuge tube to facilitate extraction.

The following invention is a new method and apparatus for laser microdissection that solves a number of problems of conventional laser microdissection and provides the ability to capture moisture-containing samples including live cells from cell cultures. As a practical example, this method allows for colonies of cells grown in slightly modified microtiter plates to be culled using a modified laser microdissection process.

Figure 1:
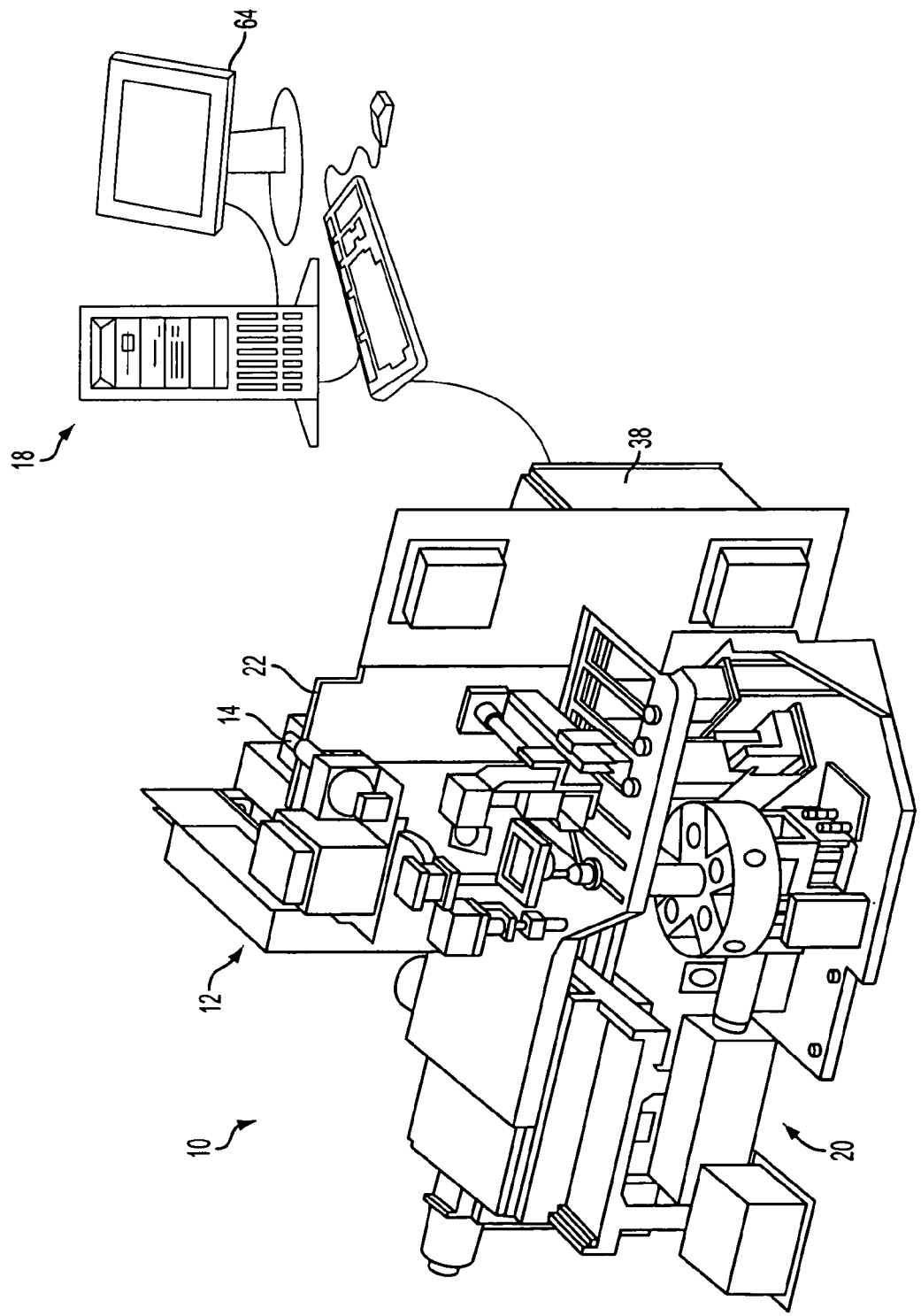
FIG. 1 illustrates a perspective view of an automated laser microdissection device.

While the invention is susceptible to various modifications and alternative forms, specific variations have been shown by way of example in the drawings and will be described herein. However, it should be understood that the invention is not limited to the particular forms disclosed. Rather, the invention is to cover all modifications, equivalents, and alternatives falling within the spirit and scope of the invention as defined by the appended claims.

DESCRIPTION OF THE INVENTION

The invention and the various features and advantageous details thereof are explained more fully with reference to the nonlimiting embodiments that are illustrated in the accompanying drawings and detailed in the following description. Descriptions of well known components and processing techniques are omitted so as not to unnecessarily obscure the invention in detail.

The entire contents of U.S. Pat. No. 6,469,779 filed Feb. 4, 1998, entitled "Laser Capture Microdissection Device"; U.S. Pat. No. 5,859,699, filed Feb. 7, 1997; U.S. Pat. No. 6,495,195, filed Feb. 14, 1997; U.S. Pat. No. 5,985,085, filed Dec. 4, 1997; and U.S. Pat. No. 6,690,470 filed Nov. 6, 2000; U.S. Patent Publication No. 2002-0090122 published Jul. 11, 2002; and PCT Publication WO 2004/025569 are hereby expressly incorporated by reference into the present application as if fully set forth herein.

A laser microdissection device operates to carry out the following general steps. A tissue or smear fixed on a standard microscope slide by routine protocols is introduced into a laser microdissection instrument. A transfer film is provided which is typically affixed to a solid substrate forming a carrier. The carrier can be of any shape. One shape for the carrier is a cap for conveniently introducing a sample into a vessel, such as a microcentrifuge tube, and sealing the vessel. The words "cap" and "carrier" are used interchangeably and it is understood by one skilled in the art that the carrier can be of any shape even where the term "cap" is employed.

The tissue sample mounted on a substrate surface is placed adjacent a transfer film carrier cap which further ensures that transfer film stays out of contact with the tissue at this stage. Alternatively, the transfer film carrier can be brought into contact with the tissue. Upon visualizing the tissue by a microscope, a user may select a region for microdissection. The selected section of the tissue is captured by pulsing at least one region of the transfer film with a low power infrared laser which activates the transfer film which then expands down into contact with the tissue. The at least one activated region of the transfer film adheres to the at least one identified portion of desired cell(s) of the tissue sample. Microdissection is completed by lifting the transfer film carrier, with the desired cell(s) attached to the film surface while the surrounding tissue remains intact. Extraction and subsequent molecular analysis of the cell contents, DNA, RNA or protein, are then carried out by standard methods.

Laser microdissection employs a polymer transfer film that is placed on top of the tissue sample. The transfer film may or may not contact the tissue sample. This transfer film is typically a thermoplastic manufactured containing organic dyes that are chosen to selectively absorb in the near infrared region of the spectrum overlapping the emission region of common AlGaAs infrared laser diodes. When the film is exposed to the focused laser beam the exposed region is heated by the laser and melts, adhering to the tissue in the region that was exposed. The film is then lifted from the tissue and the selected portion of the tissue is removed with the film. Thermoplastic transfer films such as a 100 micron thick ethyl vinyl acetate (EVA) film available from Electroseal Corporation of Pompton Lakes, N.J. (type E540) have been used in LCM applications. The film is chosen due to its low melting point of about 90° C.

A laser microdissection instrument 10 generally comprises a microscope 12, an infra-red (IR) laser source 14, an ultraviolet (UV) laser source 16, and a computer 18 as shown in FIG. 1. The IR laser source 14 and the UV laser source 16 are connected to the microscope 12 and the microscope 12 is connected to the computer 18. The instrument 10 may also include a fluorescence system 20. The computer 18 receives input and controls the operation of the microscope 12 lasers 14, 16 and fluorescence system 20.

Figure 2:
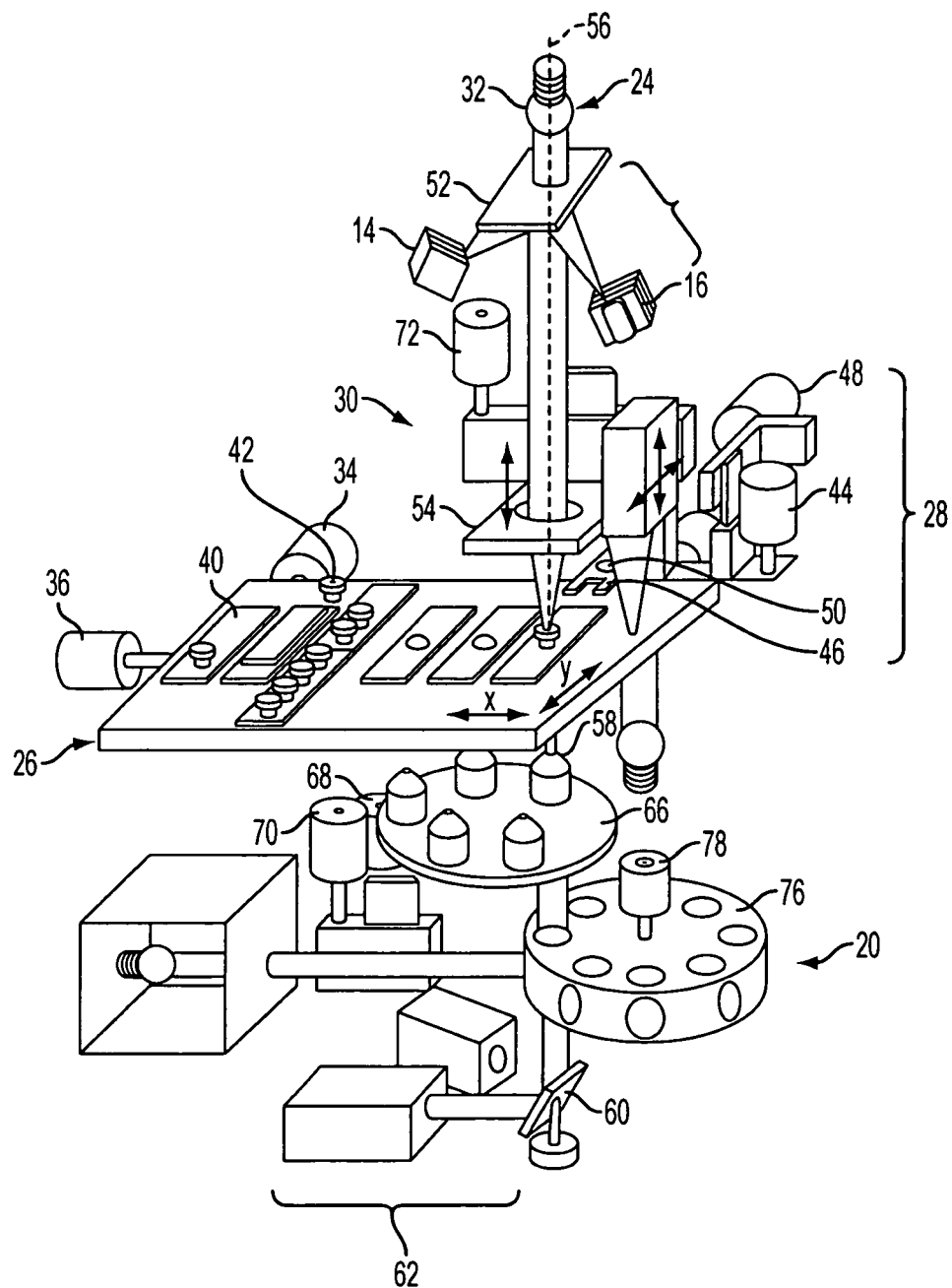
FIG. 2 illustrates a top level block diagram of the components of an automated laser microdissection device.

The microscope 12 includes an arm 22, an illumination system 24, a translation stage 26, a handling system 28 and an optical system 30 as shown in FIG. 2. The microscope arm 22 serves as a frame for carrying the components of the microscope. The illumination system 24 comprises a white light illuminator 32 such as a condenser lamp mounted on the arm. The illumination system 24, translation stage 26 and optical system 30 are arranged in an inverted transmitted-light microscope fashion such that the illumination system is arranged above the translation stage and at least one objective is arranged below the translation stage.

The translation stage 26 is also mounted on the microscope arm 22 and is adapted for receiving one or more specimens and transmitting light therethrough. A vacuum chuck may also be included to secure the specimen mounted on a specimen holder in position. The translation stage is automatically or manually movable in all directions, in particular, the planar X-Y directions. The automated translation stage includes a lateral translation motor 34 and a fore-and-aft translation motor 36 to allow complete manipulation in the X-Y plane.

The motors are controlled by a controller 38 connected to the computer which receives input such as via a mouse cursor. A mouse cursor can be used by an operator to trace a path on a visual display unit depicting a live or static image of the specimen to effect movement of the translation stage. A sophisticated road-map imaging system for navigating the specimen is described in U.S. Patent Publication No. 2002-0090122 which is incorporated herein by reference in its entirety. The translation stage provides a worksurface for handling multiple tissue samples simultaneously. The worksurface also includes a staging area 40, an output station 42 and a quality control station.

The handling system 28 is connected to the translation stage and comprises a lift fork 46. The lift fork 46 is moved in and out of the work surface by a translation motor 44 and a lift motor 48 operates to move the lift fork vertically. The lift fork is adapted to pick a carrier located at a staging or supply area of the translation stage and place the carrier in juxtaposition with the tissue specimen. When microdissection is completed, the lift fork is adapted to pick the carrier from juxtaposition with the specimen and place it in the output station where the carrier may further cap an analysis vessel. The handling system also includes a visualizer filter 50. The visualizer filter is a piece of diffuser glass positioned above tissue sample. The light from above is diffused by the visualizer filter illuminating the sample from all angles. The visualizer filter can be moved in and out of position and is located on the lift fork. The automated handling system is described in detail in U.S. Pat. No. 6,690,470 to Baer et al. and is incorporated herein by reference in its entirety.

The optical system 30 of the microscope includes several optical elements known to a person skilled in the art to make a microscope and laser microdissection instrument operate properly. These elements mounted on the microscope arm are combined to create an optical train of optical elements for pathing light. The optical system includes but is not limited to the following optical elements: mirror(s), dichroic mirror(s), lens(es), objective, beam-diameter adjuster, cut-off filter, diffuser, condenser, eyepiece and image acquisition system such as a camera.

The optical system together with its optical elements are arranged such that white light from the illumination system passes down toward the translation stage. The white light passes a condenser (not shown), dichroic mirror 52 and a focusing lens 54. The white light passes through the translation stage along a primary optical axis 56 and enters an objective 58 located beneath the translation stage 26. White light from the objective is then reflected by one or more mirrors to an eyepiece (not shown) and/or an image acquisition system 62. The live image captured by the image acquisition system is transmitted to the computer and displayed on a visual display unit 64. Static images may also be taken by the image acquisition system. A cut-off filter is typically located between the objective and the image acquisition system or eyepiece. A diffuser and a beam diameter adjuster (not shown) may also be incorporated in the optical train and located between the dichroic mirror and the translation stage. A series of microscope objectives may be selectably deployed from an objective turret wheel 66 which is controlled by an objective wheel motor 68 while a second objective focus motor 70 operates to adjust the foci of objectives which have been positioned. One skilled in the art will understand that the optical elements may be arranged in various ways for optimum performance.

Connected to the microscope is an infrared (IR) laser source 14. The IR laser source is typically a AlGaAs laser diode having a wavelength of approximately 810 nanometers. The thermoelectric cooled laser diode with collimating optics emits a beam of IR laser light that is incident upon the dichroic mirror 52. The infrared laser beam enters the optical train at the dichroic mirror and is reflected downward through the focusing lens 54 and/or beam diameter adjuster toward the translation stage. Simultaneously, the dichroic mirror allows white light from the illumination system to also pass toward the translation stage resulting in the IR laser beam and the white light illumination being superimposed along the primary optical axis 56. A laser focus motor 72 which is connected to the controller 38 and computer 18 operates to control the focusing lens and adjust the IR laser beam spot size. The computer also delivers signals to the laser via the controller to initiate IR laser pulses, adjust beam size and control IR laser power.

The IR laser operates in two modes, idle mode and pulse mode. In idle mode, the IR laser beam path provides a visible low amplitude signal that can be detected via the image acquisition system when a visual alignment of the laser spot with a portion of tissue is desired. In pulse mode, the IR laser beam path delivers energy for microdissection and the optical characteristics of a cut-off filter attenuate the IR laser beam path sufficiently such that substantially none of the energy from the IR laser beam exits through the microscope.

Suitable laser pulse widths are from 0 to approximately 1 second, preferably from 0 to approximately 100 milliseconds, more preferably approximately 50 milliseconds. In one variation, the spot size of the laser at the transfer film is variable from 0.1 to 100 microns, from 1 to 60 microns, or from 5 to 30 microns. From the standpoint of the clinical operator, the widest spot size range is the most versatile. A lower end point in the spot size range on the order of 5 microns is useful for transferring single cells.

Suitable lasers can be selected from a wide power range. For example, a 100 watt laser can be used. On the other hand, a 50 mW laser can be used. The laser can be connected to the rest of the optical subsystem with a fiber optical coupling. Smaller spot sizes are obtainable using diffraction limited laser diodes and/or single mode fiber optics. Single mode fiber allows a diffraction limited beam.

While the laser diode can be run in a standard mode such as $TEM_{00}$, other intensity profiles can be used for different types of applications. Further, the beam diameter could be changed with a stepped lens (not shown) placed in the lens assembly. Changing the beam diameter permits the size of the portion of the transfer film that is activated to be adjusted. Given a tightly focused initial condition, the beam size can be increased by defocusing. Given a defocused initial condition, the beam size can be decreased by focusing. The change in focus can be in fixed amounts. Furthermore, the change in focus can be obtained by means of indents on a movable lens mounting and/or by means of optical glass steps. In any event, increasing or decreasing the optical path length is the effect that is needed to alter the focus of the beam, thereby altering the spot size. For example, inserting a stepped glass prism into the beam so the beam strikes one step tread will change the optical path length and alter the spot size.

Also, connected to the microscope is an ultraviolet (UV) laser source 16. The UV laser source emits a beam of laser light that is incident upon the same or other dichroic mirror 52. The UV laser light enters the optical train at the dichroic mirror and is reflected downward through the focusing lens and/or beam diameter adjuster toward the translation stage. Simultaneously, the dichroic mirror allows white light from the illumination system to also pass toward the translation stage resulting in the UV laser beam and the white light illumination being superimposed along the primary optical axis. Alternatively, the UV laser can be positioned beneath the translation stage and directed through the objective along the primary axis and toward the specimen resting on the translation stage. The laser focus motor 72, which is connected to the controller and computer, operates to control the focusing lens and adjust the UV laser beam spot size. The computer also delivers signals to the UV laser via the controller to initiate UV laser pulses, change beam diameter and control UV laser power. UV laser pulse widths and beam diameter can be changed in the same manner as described above with respect to the IR laser source.

Another component connected to the microscope is a fluorescence system 20. The fluorescence system is adapted for automated selection of cells or specific regions of a sample for microdissection using fluorescently-stained tissue samples. In image analysis, the fluorescently-labeled tissue is placed in a microdissection instrument and with the fluorescent system, the cells are detected through an analysis of the image formed by the microscope. Image analysis is known in the art and is also described in detail in WO 2004/025569 which is herein incorporated by reference in its entirety.

The fluorescence system 20 includes a fluorescence excitation light source, for example, a xenon or mercury lamp 74, which emits a specific wavelength or wavelength range. The specific wavelength or wavelength range of a beam emitted by the light source is selected by a fluorescence filter wheel 76 operated by a fluorescence filter changer motor, to excite a fluorescent system (chemical markers and optical filtering techniques that are known in the industry) that is incorporated in or applied to the sample to be microdissected. The wavelength range transmitted from the excitation light source can be selected. The sample includes at least one member selected from the group consisting of chromophores and fluorescent dyes (synthetic or organic), and the process of operating the instrument includes identifying at least a portion of the sample with light that excites at least one member, before the step of transferring a portion of the sample to the laser microdissection transfer film. The fluorescent laser beam can be made coincident or coaxial with both the IR/UV laser beam path and the white light from illuminator path. Fluorescence emitted by the sample is amplified by an objective changer 66, reflected by a camera changer mirror and captured for live viewing by the acquisition system which comprises a camera. An objective changer motor and a focus motor operate to adjust the fluorescent laser beam and the emitted fluorescent beam. Optionally the objective changer may be implemented in the form of a wheel to accommodate a multiplicity of objectives (five objectives, as depicted) for providing different amplifications of the fluorescent image for the cameras. A more detailed exposition of automated fluorescent laser microdissection is found in U.S. Pat. No. 6,690,470 which is incorporated herein by reference in its entirety.

Method 1

Figure 3A:
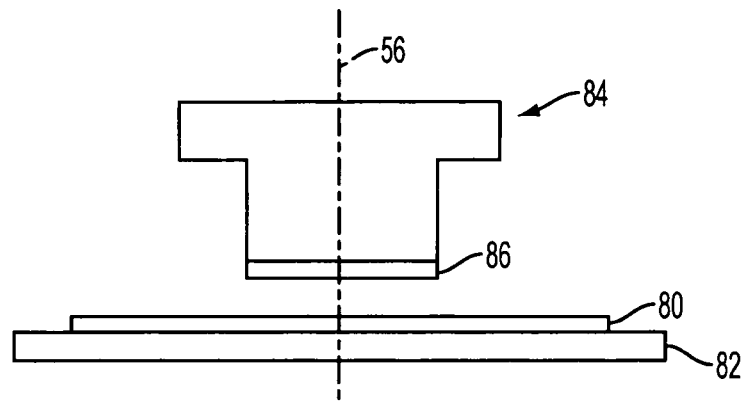
FIG. 3a illustrates a side elevation view of a transfer film carrier spaced from a tissue sample.

With reference also to FIG. 3, a sample 80 of biological material to be microdissected is applied to a substrate 82 such as a glass slide using routine protocols. The substrate with the sample affixed thereto is inserted into the laser microdissection instrument and positioned in the optical axis 56.

Figure 3B:
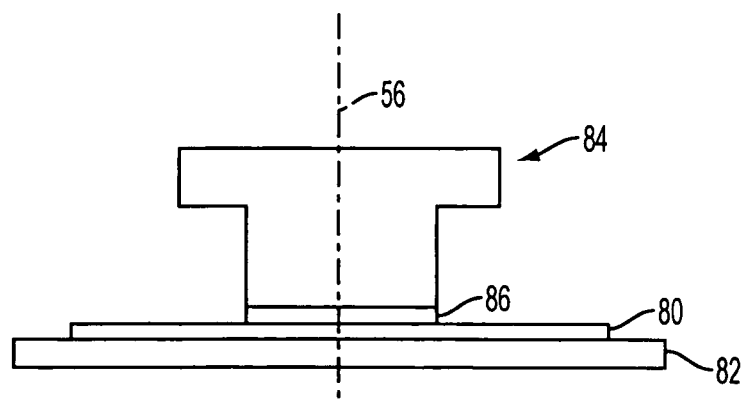
FIG. 3b illustrates a side elevation view of a transfer film carrier in contact with a tissue sample.
Figure 3C:
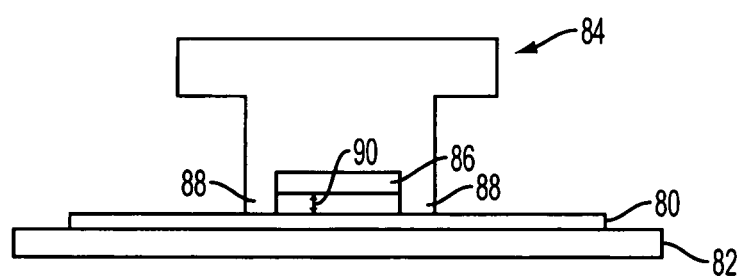
FIG. 3c illustrates a side elevation view of a transfer film carrier with standoffs in juxtaposition with a tissue sample.

The handling system 28 is used to bring a carrier 84 with a transfer film 86 affixed to its surface also into the optical axis 56 and in juxtaposition to the sample. The carrier is placed in contact with the sample such that the transfer film contacts the biological material substantially across the entirety of the transfer film surface as shown in FIG. 3*b*. Alternatively, as shown in FIG. 3*c*, the carrier is formed with standoffs 88 such that a substantial portion of the transfer film 86 does not contact the biological material 80 but remains spaced a distance 90 from the sample 80. Standoffs are described in U.S. patent application Ser. No. 08/984,979 which is herein incorporated by reference in its entirety. Standoffs are structural features that protrude from the surface of the carrier on the side of the transfer film to provide a spacing between the transfer film and the sample in order to avoid transfer of unwanted friable biological material that would otherwise adhere to the transfer film due to electrostatic forces and the like.

With the sample in the optical axis, the illumination system 24 is activated shedding light on the sample. The white light penetrating the sample arrives at the objective and is directed to the acquisition system and/or eyepiece. A live image that is captured by the acquisition system is displayed on the computer monitor. Also, a static image of relatively lower magnification is captured so as to provide a roadmap image for navigating the sample space. The two images are displayed side-by-side to locate the user on the sample space map and simultaneously provide a display of the local sample space having a relatively larger magnification. The operator inspects the sample by moving the translation stage via computer inputs, controllers and appropriate software. For example, navigation of the sample space is accomplished by tracing a path on the displayed monitor image using an input cursor via a mouse, joystick or other input means.

Figure 4A:
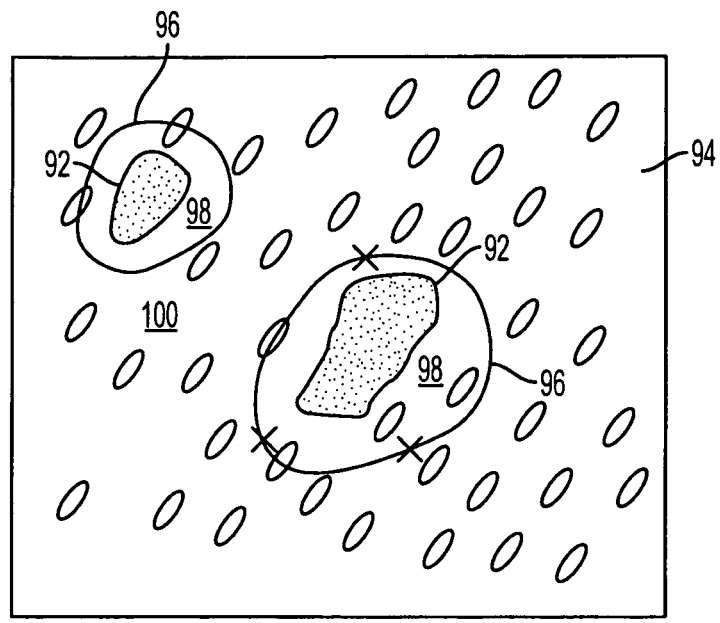
FIG. 4a illustrates a top planar view of a biological sample with targeted portions encompassed by traces.

Referring now to FIG. 4, a targeted portion 92 of biological material 94 is identified either manually by the operator or automatically employing software for algorithmic identification of regions of interest. Typically, fluorescent systems are employed for assisting the automated identification of targeted portions of biological material. Manually, the user can trace a targeted portion 92 of biological material viewed on the display monitor by moving a mouse cursor. Each trace 96 defines an interior 98 and an exterior 100. The interior 98 includes the targeted portion(s) and the exterior 100 of the trace includes non-targeted biological material. One or more targeted portions of biological material can be traced and the trace can be of any shape and size as shown in FIG. 4*a*.

Figure 4B:
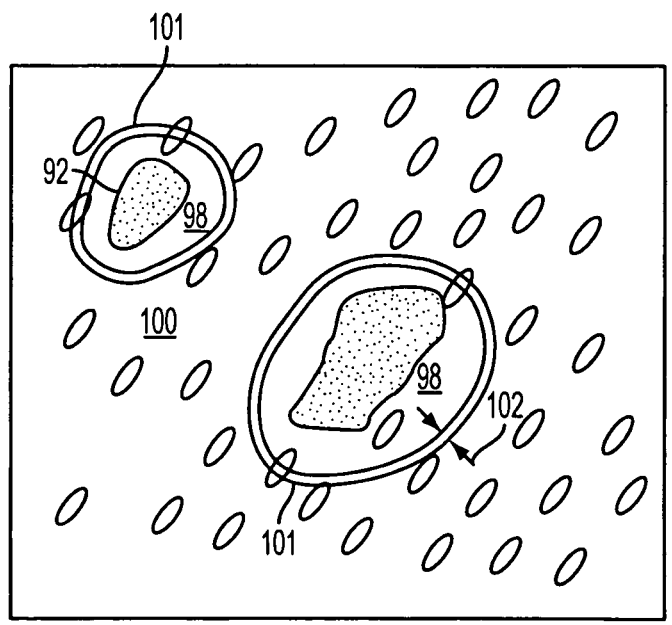
FIG. 4b illustrates a top planar view of a biological sample with targeted portions encompassed by cut paths.
Figure 4C:
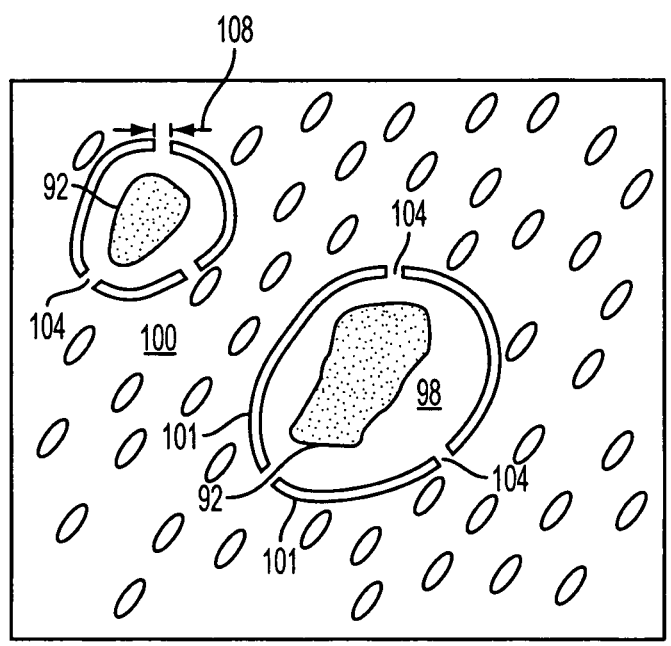
FIG. 4c illustrates a top planar view of a biological sample with targeted portions encompassed by cut paths that are interspersed with bridges.

The trace defines a cut line for the UV laser source. After all of the targeted portions 92 have been traced the user is prompted by the computer to commence cutting the traces with the UV laser source. The user may select whether each of the traces are to be closed or substantially closed paths for the UV laser. If the user selects closed paths, the UV laser source is automatically directed and activated to cut along the traces at a predefined cut width 102 forming a cut path 101 as shown in FIG. 4*b*. If the user selects a substantially closed path, at least one bridge 104 spanning from the interior 98 to the exterior 100 will be formed such that the interior 98 is joined to the surrounding exterior 100 biological material at the location of the bridge 104 as shown in FIG. 4*c*. The cut path 101 is interspersed with bridges 104 formed when the UV laser beam is temporarily de-activated while moving along a trace. The bridge width 108 can be selected by the user or predetermined by controlling software. Bridge locations may be user-defined by clicking with the mouse cursor along the trace at locations where bridges are desired as shown by the "x" in FIG. 4*a*. The user thereby manually selects any number and location of the bridges. Alternatively, the computer may automatically form a predefined number of bridges. The UV laser is activated and the biological material is eroded along the cut path but at bridge locations, biological material remains intact.

During the cutting operation of the UV laser, the laser beam remains stationary and the translation stage serves as a cut line control unit and generates, during the cutting operation, a relative movement between the laser beam and the sample. Alternatively, the cut line control unit comprises a laser scanning device which moves the laser beam relative to the stationary sample during cutting. In such an operation, the translation stage with the sample is not displaced during cutting but remains fixed in the optical axis. The cut line results exclusively from deflection of the laser beam over the sample.

Typically, after the UV laser has cut the biological material along one or more of the trace paths 96, the IR laser is directed at the one or more interiors 98 of the trace paths 96. The IR laser 14 is fired or pulsed at an interior 98 to activate the transfer film layer in the location of the interior which then adheres to the interior portion of the biological material. If a carrier with standoffs is being employed, the activated transfer film bridges the distance 90 of the standoffs 88 to contact and adhere to the interior of biological material. An IR laser pulse showing a location of adhesion to the interior of biological material is shown as a circle 106 in FIG. 5a.

Figure 5A:
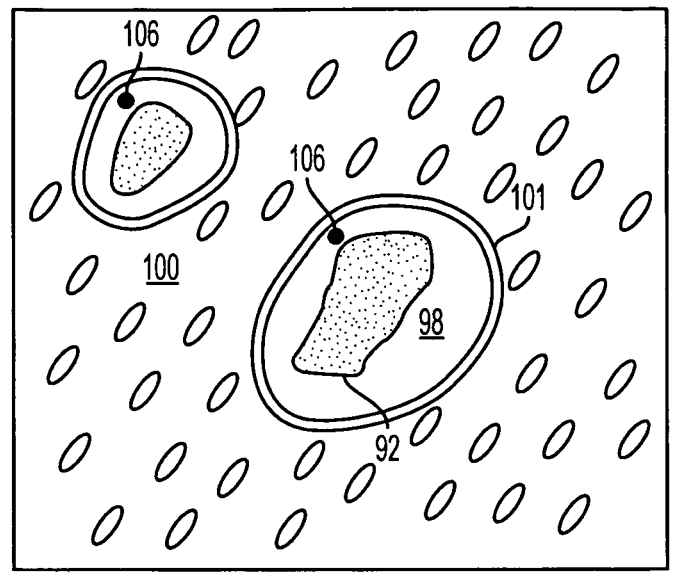
FIG. 5a illustrates a top planar view of a biological sample with infrared laser shots located interior of the cut paths.
Figure 5B:
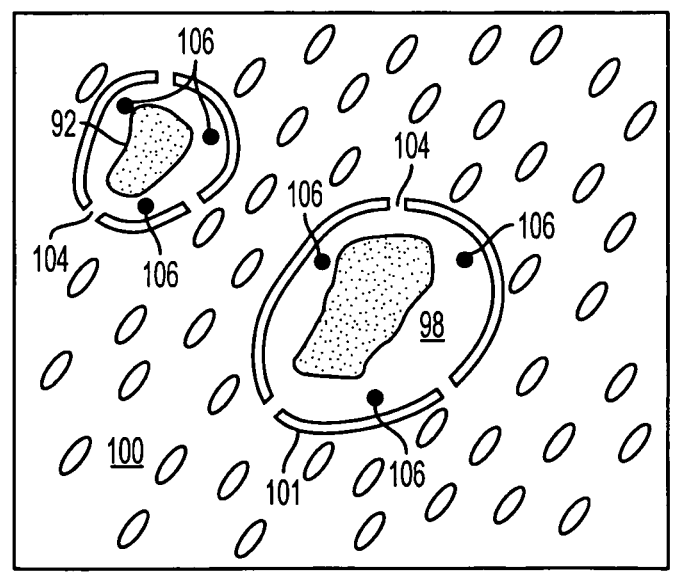
FIG. 5b illustrates a top planar view of a biological sample with infrared laser shots located in between the bridges.

The IR laser can be fired once to create a single area of adhesion or the IR laser can be fired more than once to create more than one area of adhesion on any one interior portion of biological material. The single IR laser shot can be directed in the center of the interior. In another variation, the IR laser shot can be directed at the interior of the trace but at a portion of the interior that was not targeted as desirable biological material as shown in FIG. 5a. In essence, if there is a portion of the interior which contains biological material that is not considered to be a choice selection or otherwise not targeted as desirable, the IR laser can be strategically directed at such a location to advantageously avoid raising the temperature of desired biological material in the area of the IR laser shot which would result from localized heating. If bridges are left by the UV laser trace, IR laser shots shown as circles 106 on FIG. 5b can be directed in between the bridge locations so that such points of adhesion would assist in the breaking of the bridges when the carrier is lifted away. Also, the IR laser shots can be directed at or in the proximity of the bridge locations.

If the IR laser shots are delivered manually, a user can, for example, click with a mouse cursor at a location where the user desires an IR laser shot to be located. Also, the user may select the number of IR laser shots that are to be made by clicking with a mouse cursor more than once.

If the IR laser shots are delivered automatically, computer software is programmed by the user beforehand or determined automatically to carry out one or more IR laser shots in a uniform or non-uniform pattern of IR laser shots across the interior of a trace. Of course, a single IR laser shot as well as a strategically placed IR laser shot can also be carried out automatically by the computer.

Figure 5C:
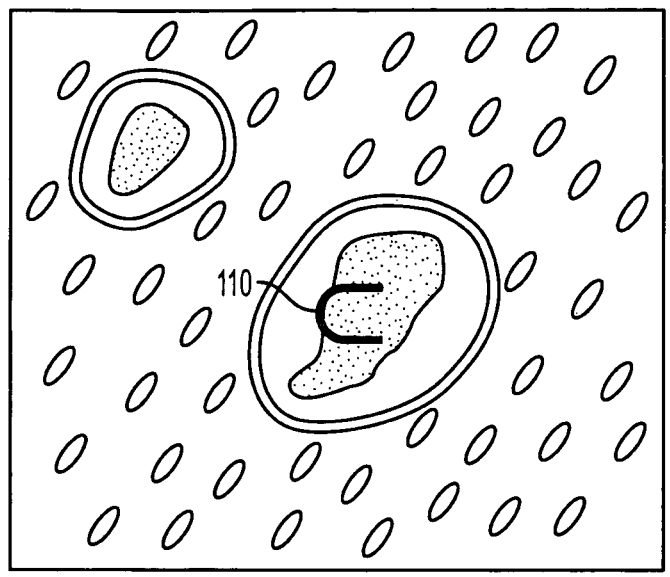
FIG. 5c illustrates a top planar view of a biological sample with an infrared laser path that is curved across the interior of a cut path.

Furthermore, the IR laser shot is not limited to being a single pulse to create a single point of adhesion. Alternatively, the IR laser can be fired with multiplicity or at duration to trace a IR path 110 of adhesion of any shape within the interior as shown in FIG. 5c. The IR laser path of adhesion is carried out in the same manner as the UV laser path of cutting. Either the translation stage is moved to create a path or the IR laser beam is directed across the interior with the translation stage remaining stationary. Basically, the number of IR laser shots, the shape of the IR laser shots and their location are not limited and any number, pattern, location or shape of IR laser shots is within the scope of the invention. Furthermore, the IR laser shot or shots can be fired before the UV laser is activated to cut the biological material.

Figure 6:
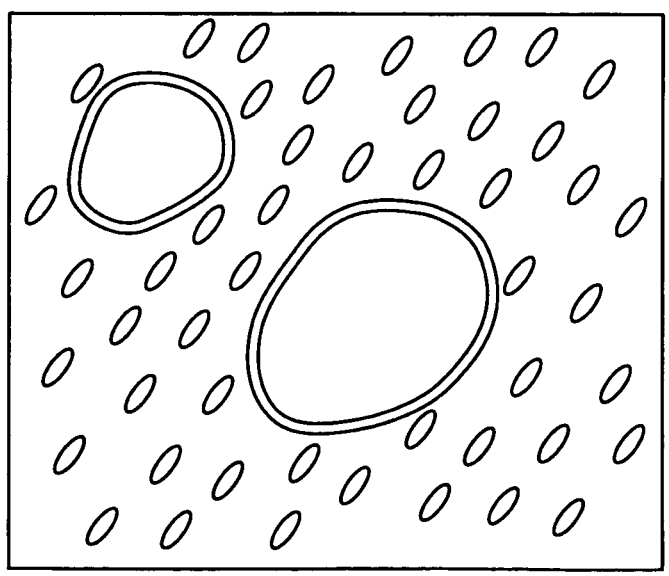
FIG. 6 illustrates a top planar view of a biological sample with targeted portions of biological material removed.
Figure 7:
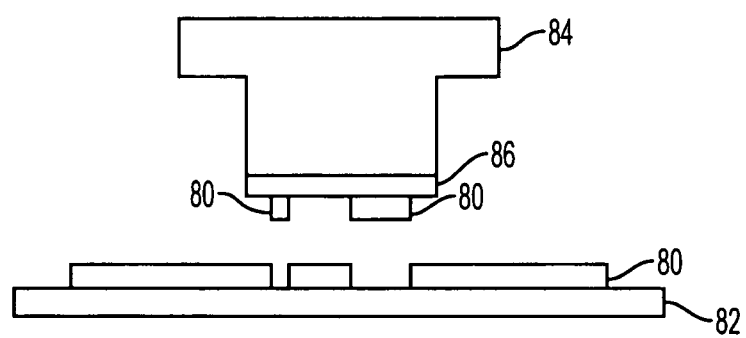
FIG. 7 illustrates a side elevation view of a transfer film carrier with targeted portions adhered thereto and separated from the remaining tissue sample.

The carrier with the transfer film will result in one or more areas of adhesion located in the one or more interiors of the UV laser cut paths. When the carrier is removed by lifting it vertically, the carrier with its attached transfer film and at least one adhered targeted portion of biological material is separated from the remaining layer of biological material. If bridges were formed, those bridges are mechanically broken upon lifting the carrier to free the adhered portions of targeted biological material. What remains is un-targeted biological material as shown in FIGS. 6 and 7. Being adhered to the transfer film, the targeted biological material is removed with the carrier and available for further processing.

Method 2

With reference also to FIG. 8, a sample 80 of biological material to be microdissected is applied to a membrane 81. The membrane 81 is typically a polymer membrane such as a polyester. The polymer membrane is thin enough to maximize the ability to capture small sections and also has enough physical integrity to be handled in the process. The membrane is selected to adhere to the transfer film in the activated region and break away from surrounding non-activated and non-selected regions. The membrane is transparent so that the tissue sample can be visualized through the membrane. Also, the membrane is selected to be compatible with the reagents used in fixing and staining biological tissue. Therefore, depending upon the selected membrane, staining protocols that may compromise lipid, carbohydrate, and other macromolecular targets are avoided. One material suitable for the membrane is polyethylene naphalate (PEN) having a thickness of approximately 1.0 to approximately 2.0 micrometers.

The membrane is typically carried by a frame 83. The frame 83 can be a framed-foil slide such as that described in WO2002/057746A2 which is incorporated herein by reference as if fully set forth herein. A framed-foil slide is simply a frame in the shape of a glass slide with a window such that the membrane is affixed to the frame with the membrane covering the window. A petrie dish with a membrane bottom and firm side walls (glass, metal or plastic) works well too. The small cavity formed by the side walls of the window of the framed slide or the petrie dish provides some depth for growing cells and adding growth medium. Various coatings such as poly-1-lysine and growth media can be added to the petrie dish or framed slide to assist in cell viability and growth. The petrie dish or framed slide can be covered with an appropriate top to provide for isolation.

The sample 80 of biological material can be prepared in all of the standard means including sectioning by microtome, smears and cytospins. The sample can also be prepared by growing cells onto the polymer film in order to harvest live cells. The tissue or cells are attached directly to the membrane layer. Tissue preparation protocols that result in strong adhesion to the polymer membrane and which allow for the microdissection of hydrated samples and live cell samples are used. Tissue preparation protocols are followed in order to assure that the tissue adheres enough to survive the liquid processing, but that the adhesion is weak enough to allow microdissection to occur. If the capture of hydrated living cells is not desired, the tissue sample is typically exposed to ethanol with diminishing levels of water and finally exposed to xylene.

Figure 8A:
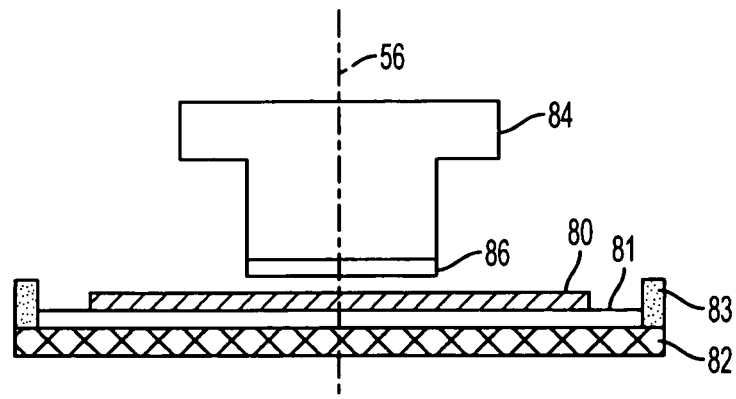
FIG. 8a illustrates a side elevation view of a transfer film carrier spaced from a tissue sample.

The membrane 81 with the sample 80 mounted on its upper surface is placed in contact with a substrate 82 such that the lower surface of the membrane contacts the upper surface of the substrate as shown in FIG. 8a. The substrate is typically a glass slide. The substrate, membrane and sample are inserted into the laser microdissection instrument and positioned in the optical axis 56.

Figure 8B:
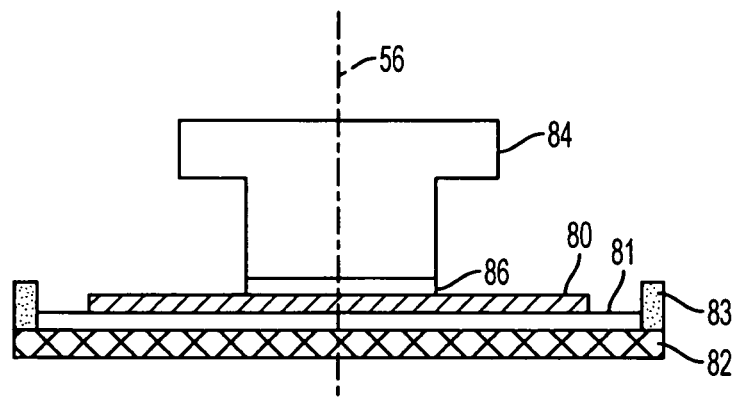
FIG. 8b illustrates a side elevation view of a transfer film carrier in contact with a tissue sample.
Figure 8C:
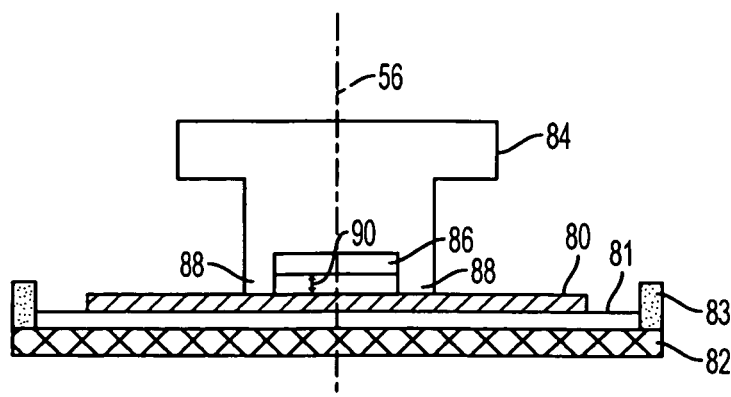
FIG. 8c illustrates a side elevation view of a transfer film carrier with standoffs in juxtaposition with a tissue sample.

The handling system 28 is used to bring a carrier 84 with a transfer film 86 affixed to its surface also into the optical axis 56 and in juxtaposition to the sample. The carrier is placed in contact with the sample such that the transfer film contacts the biological material substantially across the entirety of the transfer film surface as shown in FIG. 8b. Alternatively, as shown in FIG. 8c, the carrier is formed with standoffs 88 such that a substantial portion of the transfer film 86 does not contact the biological material 80 but remains spaced a distance 90 from the sample 80. Standoffs are described in U.S. patent application Ser. No. 08/984,979 which is herein incorporated by reference in its entirety. Standoffs are structural features that protrude from the surface of the carrier on the side of the transfer film to provide a spacing between the transfer film and the sample in order to avoid transfer of unwanted friable biological material that would otherwise adhere to the transfer film due to electrostatic forces and the like.

With the sample in the optical axis, the illumination system 24 is activated shedding light on the sample. The white light penetrating the sample arrives at the objective and is directed to the acquisition system and/or eyepiece. A live image that is captured by the acquisition system is displayed on the computer monitor. Also, a static image of relatively lower magnification is captured so as to provide a roadmap image for navigating the sample space. The two images are displayed side-by-side to locate the user on the sample space map and simultaneously provide a display of the local sample space having a relatively larger magnification. The operator inspects the sample by moving the translation stage via computer inputs, controllers and appropriate software. For example, navigation of the sample space is accomplished by tracing a path on the displayed monitor image using an input cursor via a mouse, joystick or other input means.

Figure 9A:
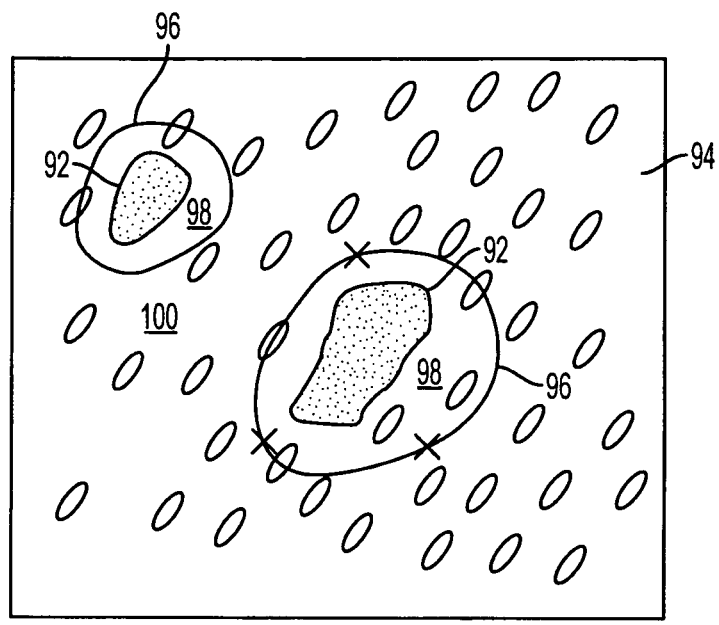
FIG. 9a illustrates a top planar view of a biological sample with targeted portions encompassed by traces.

Referring now to FIG. 9, a targeted portion 92 of biological material 94 is identified either manually by the operator or automatically employing software for algorithmic identification of regions of interest. Typically, fluorescent systems are employed for assisting the automated identification of targeted portions of biological material. Manually, the user can trace a targeted portion 92 of biological material viewed on the display monitor by moving a mouse cursor. Each trace 96 defines an interior 98 and an exterior 100. The interior 98 includes the targeted portion(s) and the exterior 100 of the trace includes non-targeted biological material. One or more targeted portions of biological material can be traced and the trace can be of any shape and size as shown in FIG. 9a.

Figure 9B:
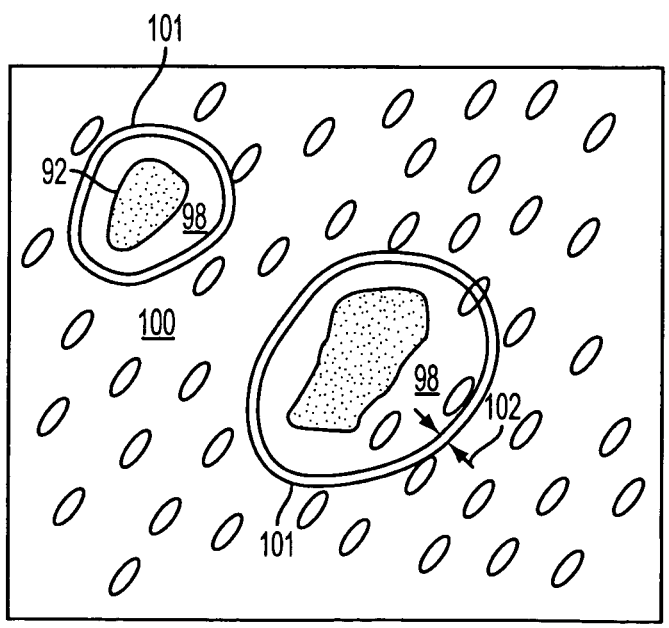
FIG. 9b illustrates a top planar view of a biological sample with targeted portions encompassed by cut paths.
Figure 9C:
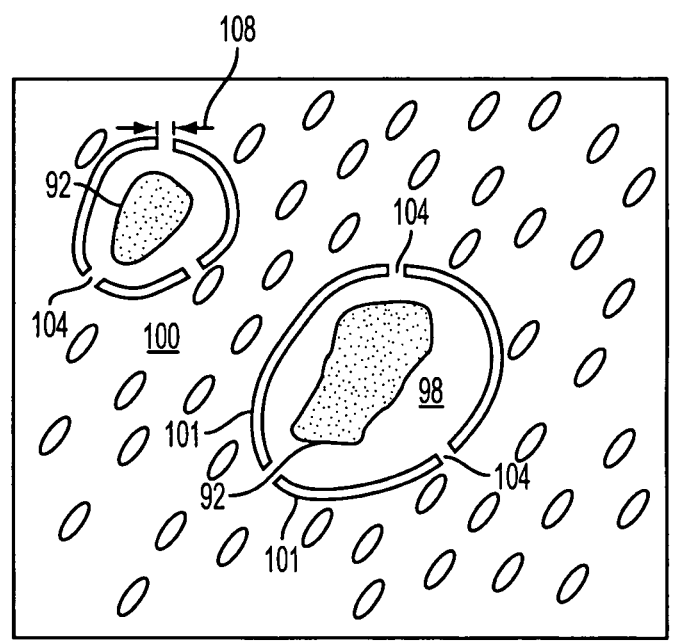
FIG. 9c illustrates a top planar view of a biological sample with targeted portions encompassed by cut paths that are interspersed with bridges.

The trace defines a cut line for the UV laser source. After all of the targeted portions 92 have been traced the user is prompted by the computer to commence cutting the traces with the UV laser source. The user may select whether each of the traces are to be closed or substantially closed paths for the UV laser. If the user selects closed paths, the UV laser source is automatically directed and activated to cut along the traces at a predefined cut width 102 forming a cut path 101 as shown in FIG. 9b. If the user selects a substantially closed path, at least one bridge 104 spanning from the interior 98 to the exterior 100 will be formed such that the interior 98 is joined to the surrounding exterior 100 biological material at the location of the bridge 104 as shown in FIG. 9c. The cut path 101 is interspersed with bridges 104 formed when the UV laser beam is temporarily de-activated while moving along a trace. The bridge width 108 can be selected by the user or predetermined by controlling software. Bridge locations may be user-defined by clicking with the mouse cursor along the trace at locations where bridges are desired as shown by the "x" in FIG. 9a. The user thereby manually selects any number and location of the bridges. Alternatively, the computer may automatically form a predefined number of bridges. The UV laser is activated and the biological material is eroded along the cut path but at bridge locations, biological material remains intact.

During the cutting operation of the UV laser, the laser beam remains stationary and the translation stage serves as a cut line control unit and generates, during the cutting operation, a relative movement between the laser beam and the sample. Alternatively, the cut line control unit comprises a laser scanning device which moves the laser beam relative to the stationary sample during cutting. In such an operation, the translation stage with the sample is not displaced during cutting but remains fixed in the optical axis. The cut line results exclusively from deflection of the laser beam over the sample. The UV laser erodes the membrane and the biological material along the cut path. The desired cells are not harmed by the UV laser shots. Also, if the UV laser is located underneath the translation stage, the membrane advantageously shields the bulk of the tissue sample from UV radiation by absorbing a portion of the radiation that would otherwise be incident upon the tissue.

Typically, after the UV laser has cut the biological material and membrane along one or more of the trace paths 96, the IR laser is directed at the one or more interiors 98 of the trace paths 96. The IR laser 14 is fired or pulsed at any location of the interior 98 to activate the transfer film layer in the location of the interior which then adheres to the interior portion of the cut path. If a carrier with standoffs is being employed, the activated transfer film bridges the distance 90 of the standoffs 88 to contact and adhere to the interior of biological material. An IR laser pulse showing a location of adhesion to the interior of biological material is shown as a circle 106 in FIG. 10a.

Figure 10A:
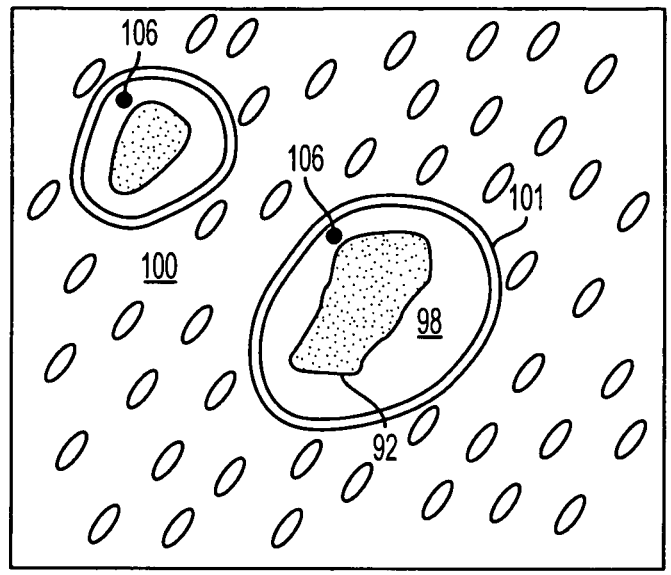
FIG. 10a illustrates a top planar view of a biological sample with infrared laser shots located interior of the cut paths.
Figure 10B:
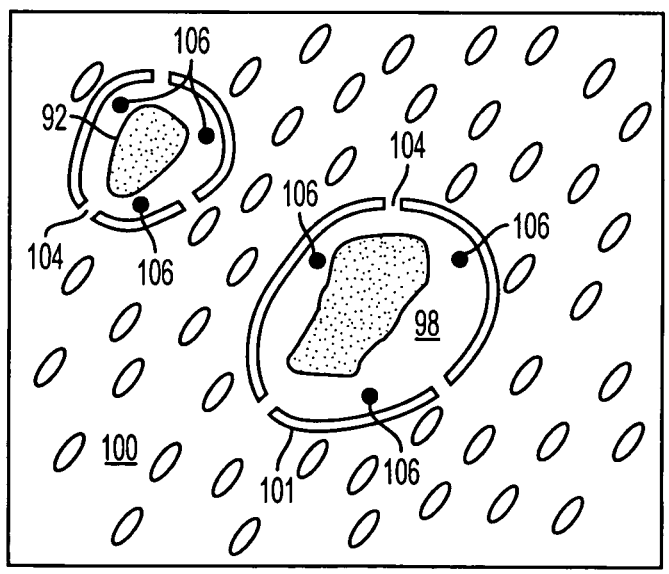
FIG. 10b illustrates a top planar view of a biological sample with infrared laser shots located in between the bridges.

The IR laser can be fired once to create a single area of adhesion or the IR laser can be fired more than once to create more than one area of adhesion on any one interior portion of biological material. The single IR laser shot can be directed in the center of the interior or along the perimeter of the cut path. In another variation, the single IR laser shot can be directed at the interior of the trace but at a portion of the interior, including an area of membrane, that was not targeted as desirable biological material as shown in FIG. 10a. In essence, if there is a portion of the interior which contains biological material that is not considered to be a choice selection or otherwise not targeted as desirable or an exposed portion of the membrane, the IR laser can be strategically directed at such a location to advantageously avoid raising the temperature of desired biological material in the area of the IR laser shot which would result from localized heating. If bridges are left by the UV laser trace, IR laser shots shown as circles 106 on FIG. 10b can be directed in between the bridge locations so that such points of adhesion would assist in the breaking of the bridges when the carrier is lifted away. IR laser shots also can be directed at or in the vicinity of the bridge locations.

If the IR laser shots are delivered manually, a user can, for example, click with a mouse cursor at a location where the user desires an IR laser shot to be located. Also, the user may select the number of IR laser shots that are to be made by clicking with a mouse cursor more than once.

If the IR laser shots are delivered automatically, computer software is programmed by the user beforehand or determined automatically to carry out one or more IR laser shots in a uniform or non-uniform pattern of IR laser shots across the interior of a trace. Of course, a single IR laser shot as well as a strategically placed IR laser shot can also be carried out automatically by the computer.

Figure 10C:
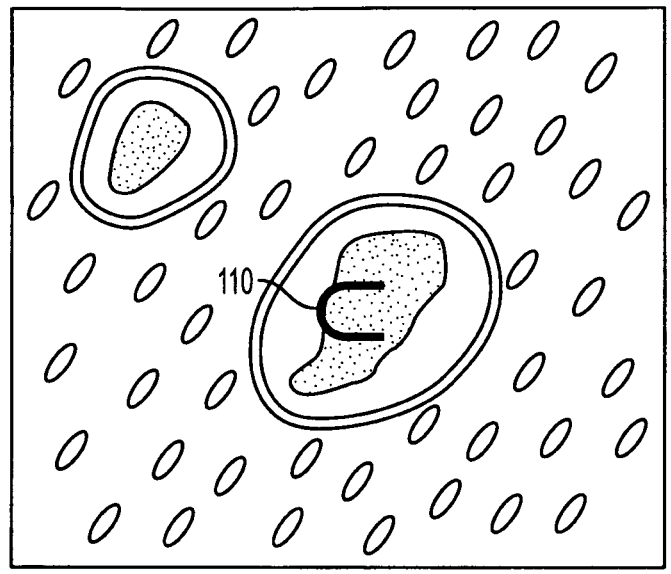
FIG. 10c illustrates a top planar view of a biological sample with an infrared laser path that is curved across the interior of a cut path.

Furthermore, the IR laser shot is not limited to being a single pulse to create a single point of adhesion. Alternatively, the IR laser can be fired at duration to trace a IR path 110 of adhesion of any shape within the interior as shown in FIG. 10c. The IR laser path of adhesion is carried out in the same manner as the UV laser path of cutting. Either the translation stage is moved to create a path or the IR laser beam is directed across the interior with the translation stage remaining stationary. Basically, the number of IR laser shots, the shape of the IR laser shots and their location are not limited and any number, location, pattern, or shape of IR laser shots is within the scope of the invention. Furthermore, the IR laser shot or shots can be fired before the UV laser is activated to cut the biological material.

Figure 11:
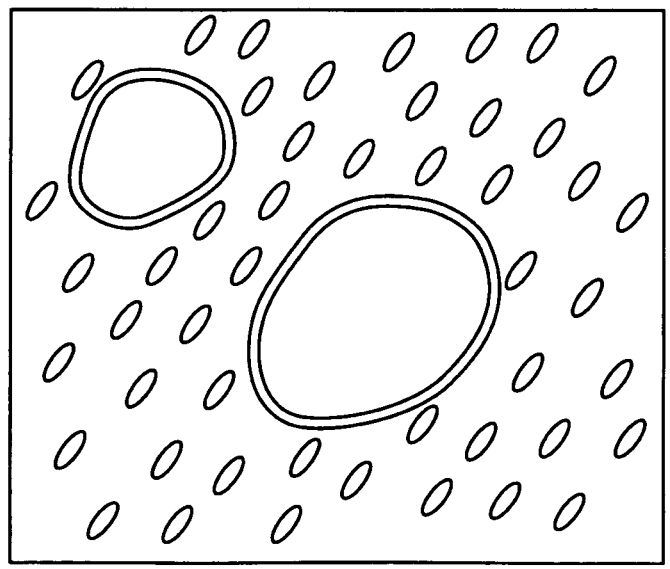
FIG. 11 illustrates a top planar view of a biological sample with targeted portions of biological material removed.
Figure 12:
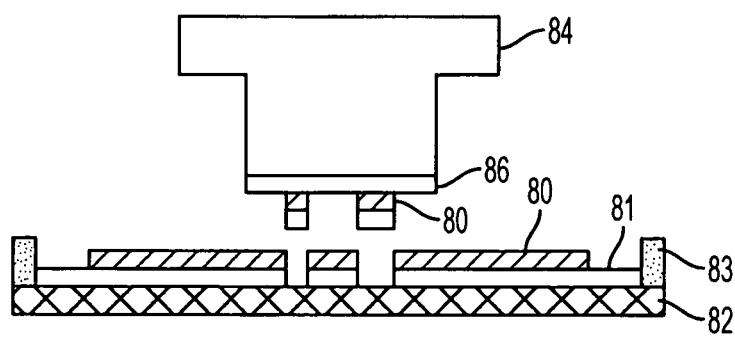
FIG. 12 illustrates a side elevation view of a transfer film carrier with targeted portions adhered thereto and separated from the remaining tissue sample.

The carrier with the transfer film will result in one or more areas of adhesion located in the one or more interiors of the UV laser cut paths. When the carrier is removed by lifting it vertically, the carrier with its attached transfer film and at least one adhered targeted portion of biological material is separated from the remaining layer of biological material. If bridges were formed, those bridges are mechanically broken upon lifting the carrier to free the adhered portions of targeted biological material. What remains is un-targeted biological material as shown in FIGS. 11 and 12. Being adhered to the transfer film, the targeted biological material is removed with the carrier and available for further processing.

Method 3

Figure 13A:
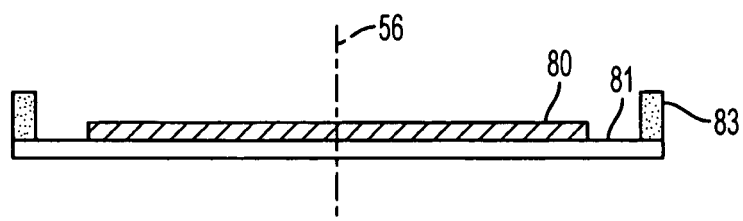
FIG. 13a illustrates a side elevation view of a tissue sample mounted on a polymer membrane connected to a frame.

With reference to FIG. 13a, a sample 80 of biological material to be microdissected is applied to a membrane 81. The membrane 81 is typically a polymer membrane such as a polyester. The polymer membrane is thin enough to maximize the ability to capture small sections and also has enough physical integrity to be handled in the process. The membrane is selected to adhere to the transfer film in the activated region and break away from surrounding non-activated and non-selected regions. The polymer membrane is transparent so that the tissue sample can be visualized through the membrane. Also, the membrane is selected to be compatible with the reagents used in fixing and staining biological tissue. Therefore, depending upon the selected membrane, staining protocols that may compromise lipid, carbohydrate, and other macromolecular targets are avoided. One material suitable for the membrane is polyethylene naphalate (PEN) having a thickness of approximately 1.0 to approximately 2.0 micrometers.

The membrane is typically be carried by a frame 83. The frame 83 can be a framed-foil slide such as that described in WO2002/057746A2 which is incorporated herein by reference as if fully set forth herein. A framed-foil slide is simply a frame in the shape of a glass slide with a window such that the membrane is affixed to the frame with the membrane covering the window. A petrie dish with a membrane bottom and firm side walls (glass, metal or plastic) works well too. The small cavity formed by the side walls of the window of the framed slide or the petrie dish provides some depth for growing cells and adding growth medium. Various coatings such as poly-1-lysine and growth media can be added to the petrie dish or framed slide to assist in cell viability and growth. The petrie dish or framed slide can be covered with an appropriate top to provide for isolation.

The sample 80 of biological material can be prepared in all of the standard means including sectioning by microtome, smears and cytospins. The sample can also be prepared by growing cells onto the polymer film in order to harvest live cells. The tissue or cells are attached directly to the membrane layer. Tissue preparation protocols that result in strong adhesion to the polymer membrane and which allow for the microdissection of hydrated samples and live cell samples are used. Tissue preparation protocols are followed in order to assure that the tissue adheres enough to survive the liquid processing, but that the adhesion is weak enough to allow microdissection to occur. If the capture of hydrated living cells is not desired, the tissue sample is typically exposed to ethanol with diminishing levels of water and finally exposed to xylene.

Figure 13B:
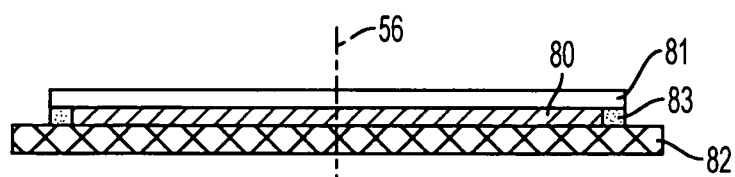
FIG. 13b illustrates a side elevation view of a tissue sample mounted on a polymer membrane connected to a frame and inverted onto a substrate.
Figure 13C:
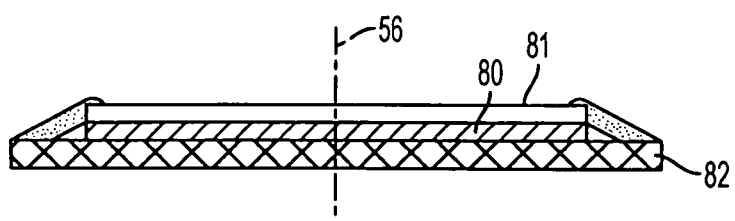
FIG. 13c illustrates a side elevation view of a tissue sample mounted on a polymer membrane and inverted onto a substrate with the polymer membrane being adhered to the substrate.

The membrane 81 with the sample 80 mounted on its upper surface is inverted and placed in contact with a substrate 82 such that the biological material 80 contacts the upper surface of the substrate 82 and the upper surface of the membrane faces the upper surface of the substrate 82 as shown in FIG. 13b. The substrate is typically a glass slide. If a frame 83 is not being using, the polymer membrane 81 is adhered to the substrate 82 as shown in FIG. 13c. The substrate, membrane and sample are inserted into the laser microdissection instrument and positioned in the optical axis 56.

Figure 13D:
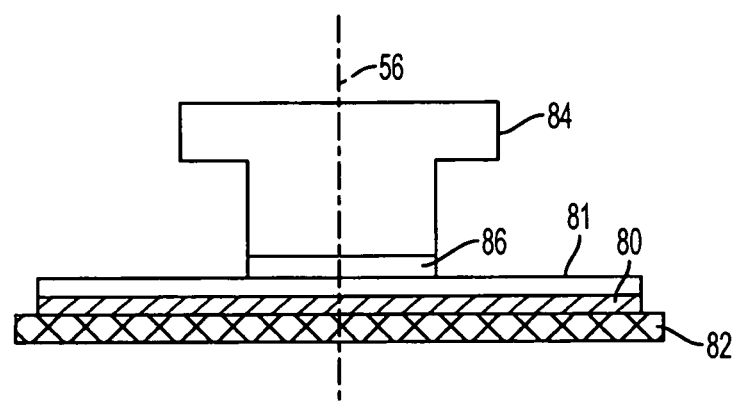
FIG. 13d illustrates a side elevation view of a transfer film carrier in contact with a membrane.
Figure 13E:
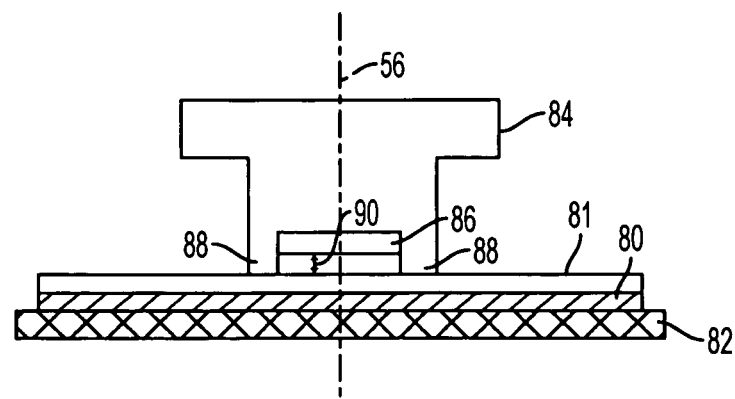
FIG. 13e illustrates a side elevation view of a transfer film carrier with standoffs in juxtaposition with the substrate.

The handling system 28 is used to bring a carrier 84 with a transfer film 86 affixed to its surface also into the optical axis 56 and in juxtaposition with the substrate 82 on the side of the membrane 81. In one variation, the carrier is placed in contact with the membrane 81 such that the transfer film 86 contacts the membrane substantially across the entirety of the transfer film surface as shown in FIG. 13d. Alternatively, as shown in FIG. 13e, the transfer film is spaced apart from the membrane. In one variation, the carrier is formed with standoffs 88 such that a substantial portion of the transfer film 86 does not contact the membrane 81 but remains spaced a distance 90 from the membrane 81. Standoffs are described in U.S. patent application Ser. No. 08/984,979 which is herein incorporated by reference in its entirety. Standoffs are structural features that protrude from the surface of the carrier on the side of the transfer film to provide a spacing between the transfer film and the membrane in order to avoid transfer of unwanted material that would otherwise adhere to the transfer film due to electrostatic forces and the like.

With the sample in the optical axis, the illumination system 24 is activated shedding light on the sample. The white light penetrating the sample arrives at the objective and is directed to the acquisition system and/or eyepiece. A live image that is captured by the acquisition system is displayed on the computer monitor. Also, a static image of relatively lower magnification is captured so as to provide a roadmap image for navigating the sample space. The two images are displayed side-by-side to locate the user on the sample space map and simultaneously provide a display of the local sample space having a relatively larger magnification. The operator inspects the sample by moving the translation stage via computer inputs, controllers and appropriate software. For example, navigation of the sample space is accomplished by tracing a path on the displayed monitor image using an input cursor via a mouse, joystick or other input means.

Figure 14A:
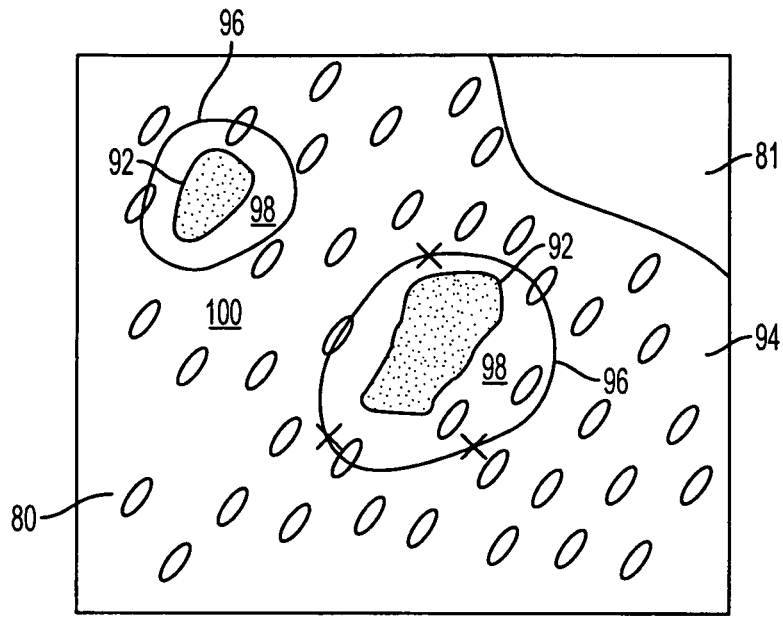
FIG. 14a illustrates a top planar sectional view of a membrane and biological sample with targeted portions encompassed by traces.

FIG. 14a illustrates a top planar sectional view of the membrane 81 and biological sample 80. A targeted portion 92 of biological material 94 is identified either manually by the operator or automatically employing software for algorithmic identification of regions of interest. Typically, fluorescent systems are employed for assisting the automated identification of targeted portions of biological material. Manually, the user can trace a targeted portion 92 of biological material viewed on the display monitor by moving a mouse cursor.

Each trace 96 defines an interior 98 and an exterior 100. The interior 98 includes the targeted portion(s) and the exterior 100 of the trace includes non-targeted biological material. One or more targeted portions of biological material can be traced and the trace can be of any shape and size as shown in FIG. 14*a*.

Figure 14B:
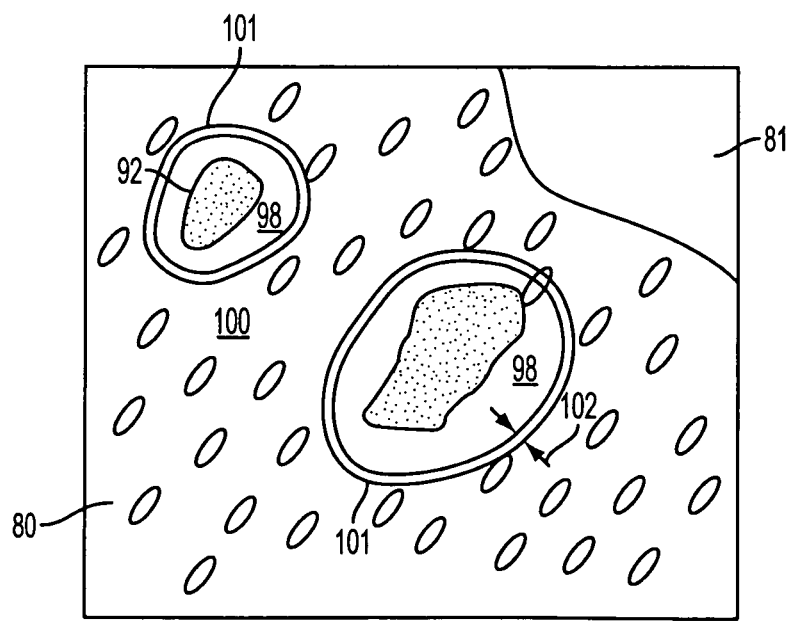
FIG. 14b illustrates a top planar sectional view of a membrane and biological sample with targeted portions encompassed by cut paths.
Figure 14C:
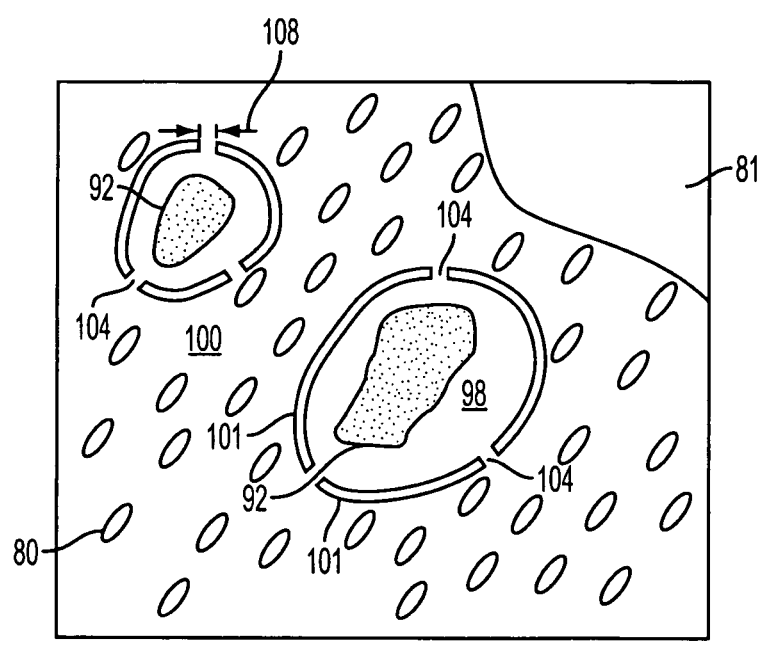
FIG. 14c illustrates a top planar view of a membrane and biological sample with targeted portions encompassed by cut paths that are interspersed with bridges.

The trace defines a cut line for the UV laser source. After all of the targeted portions 92 have been traced the user is prompted by the computer to commence cutting along the traces with the UV laser source. The user may select whether each of the traces are to be closed or substantially closed paths for the UV laser. If the user selects closed paths, the UV laser source is automatically directed and activated to cut along the traces at a predefined cut width 102 forming a cut path 101 as shown in FIG. 14*b*. If the user selects a substantially closed path, at least one bridge 104 spanning from the interior 98 to the exterior 100 will be formed such that the interior 98 is joined to the surrounding exterior 100 at the location of the bridge 104 as shown in FIG. 14*c*. The cut path 101 is interspersed with bridges 104 formed when the UV laser beam is temporarily de-activated while moving along a trace. The bridge width 108 can be selected by the user or predetermined by controlling software. Bridge locations may be user-defined by clicking with the mouse cursor along the trace at locations where bridges are desired as shown by the "x" in FIG. 14*a*. The user thereby manually selects any number and location of the bridges. Alternatively, the computer may automatically form a predefined number of bridges. The UV laser is activated and the biological material and membrane is eroded along the cut path but at bridge locations, biological material and membrane remain intact.

During the cutting operation of the UV laser, the laser beam remains stationary and the translation stage serves as a cut line control unit and generates, during the cutting operation, a relative movement between the laser beam and the sample. Alternatively, the cut line control unit comprises a laser scanning device which moves the laser beam relative to the stationary sample during cutting. In such an operation, the translation stage with the sample is not displaced during cutting but remains fixed in the optical axis. The cut line results exclusively from deflection of the laser beam over the sample. The UV laser erodes the membrane and the biological material along the cut path. The desired cells are not harmed by the UV laser shots. Also, if the UV laser is located above the translation stage, the membrane advantageously shields the bulk of the tissue sample from UV radiation by absorbing a portion of the radiation that would otherwise be incident upon the tissue.

Figure 15A:
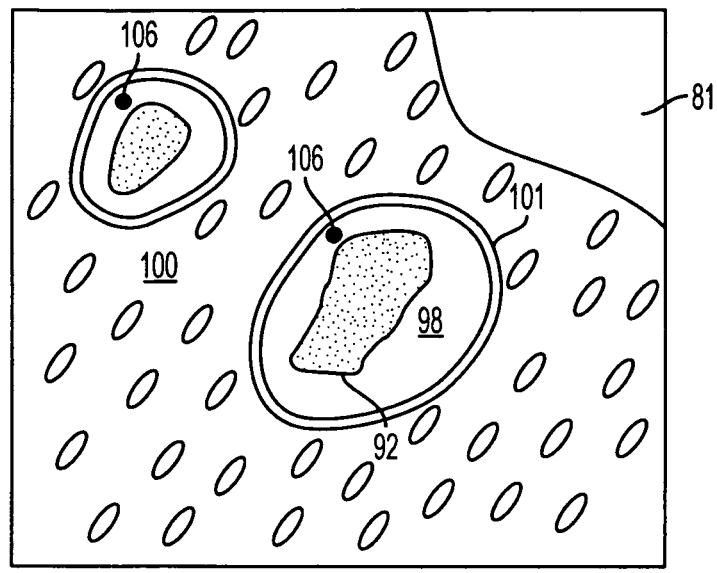
FIG. 15a illustrates a top planar sectional view of a membrane and biological sample with infrared laser shots located interior of the cut paths.

Typically, after the UV laser has cut the biological material and membrane along one or more of the trace paths 96, the IR laser is directed at the one or more interiors 98 of the trace paths 96. The IR laser 14 is fired or pulsed at any location of the interior 98 to activate the transfer film layer in the location of the interior which then adheres onto the membrane. If a carrier with standoffs is being employed, the transfer film carrier remains in a fixed position relative to the membrane. With the carrier remaining fixed, the transfer film is brought into contact with the membrane. The activated transfer film bridges the distance 90 of the standoffs 88 to contact and adhere to the membrane in the interior of the cut path. The location of an IR laser pulse is shown as a circle 106 at the interior of the cut path in FIG. 15*a*.

Figure 15B:
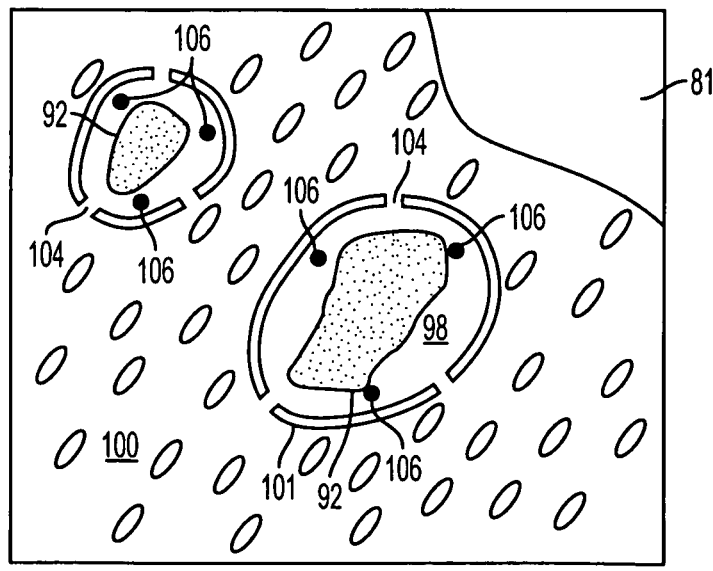
FIG. 15b illustrates a top planar sectional view of a membrane and biological sample with infrared laser shots located in between the bridges.

The IR laser can be fired once to create a single area of adhesion or the IR laser can be fired more than once to create more than one area of adhesion on any one interior portion of the membrane. The single IR laser shot can be directed in the center of the interior or along the perimeter of the cut path. The membrane advantageously diminishes raising the temperature of desired biological material in the area of the IR laser shot which would result from localized heating. If bridges are left by the UV laser trace, IR laser shots shown as circles 106 on FIG. 15*b* can be directed in between the bridge locations or in the vicinity of the bridges so that such points of adhesion would assist in the breaking of the bridges when the carrier is lifted away. Also, IR shots can be directed at the bridge locations or in the vicinity of the bridges.

If the IR laser shots are delivered manually, a user can, for example, click with a mouse cursor at a location where the user desires an IR laser shot to be located. Also, the user may select the number of IR laser shots that are to be made by clicking with a mouse cursor more than once. If the IR laser shots are delivered automatically, computer software is programmed by the user beforehand or determined automatically to carry out one or more IR laser shots in a uniform or non-uniform pattern of IR laser shots across the interior of a trace.

Figure 15C:
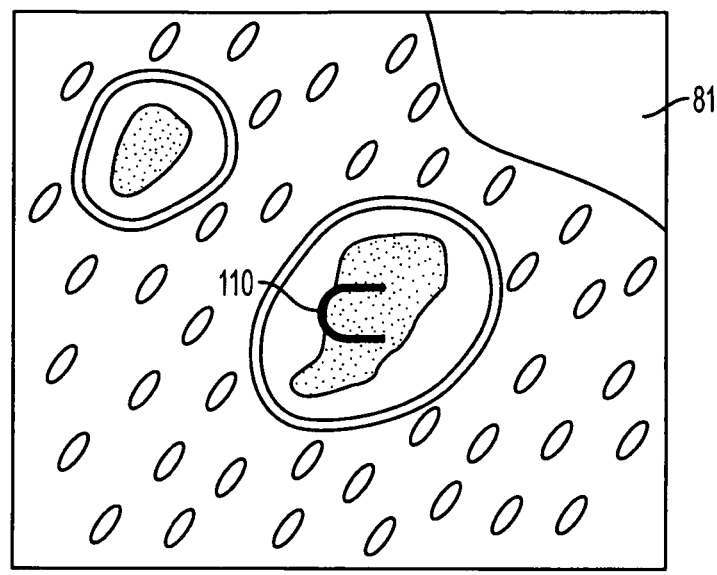
FIG. 15c illustrates a top planar sectional view of a membrane and biological sample with an infrared laser path that is curved across the interior of a cut path.

Furthermore, the IR laser shot is not limited to being a single pulse to create a single point of adhesion to the membrane. Alternatively, the IR laser can be fired at duration to trace a IR path 110 of adhesion of any shape within the interior as shown in FIG. 15*c*. The IR laser path of adhesion is carried out in the same manner as the UV laser path of cutting. Either the translation stage is moved to create a path or the IR laser beam is directed across the interior with the translation stage remaining stationary. Basically, the number of IR laser shots, the shape of the IR laser shots and their location are not limited and any number, location, pattern, or shape of IR laser shots is within the scope of the invention. Furthermore, the IR laser shot or shots can be fired before the UV laser is activated to cut the membrane and biological material.

Figure 16:
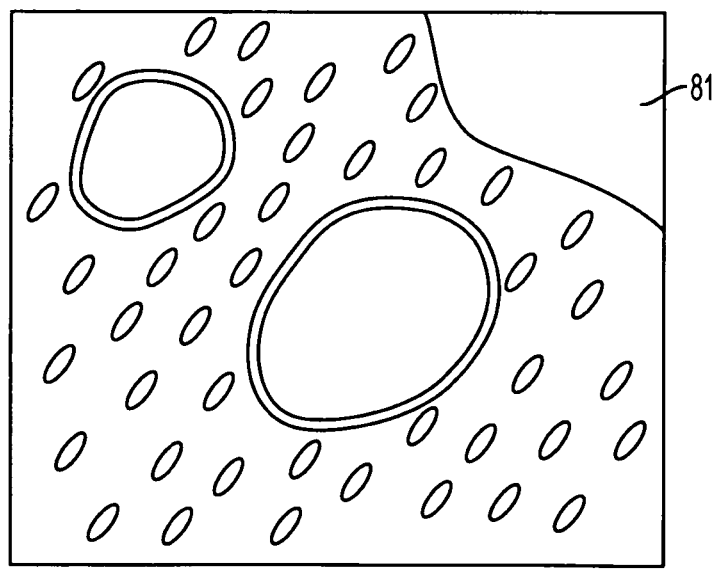
FIG. 16 illustrates a top planar sectional view of a membrane and biological sample with targeted portions of biological material removed.
Figure 17:
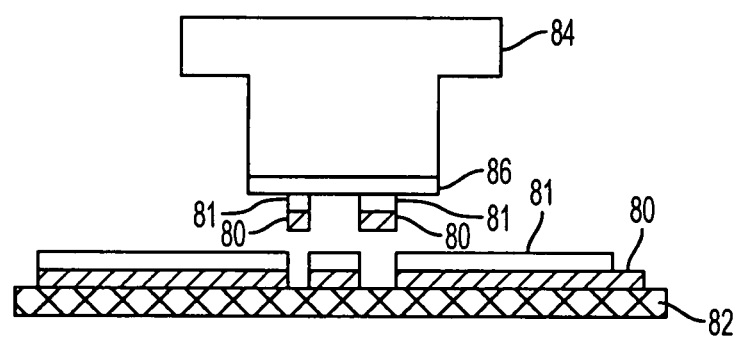
FIG. 17 illustrates a side elevation view of a transfer film carrier with targeted portions adhered thereto and separated from the remaining tissue sample.

The carrier with the transfer film will result in one or more areas of adhesion with the membrane located in the one or more interiors of the UV laser cut paths. When the carrier is separated by lifting it vertically, the carrier with its attached transfer film and at least one adhered portion of membrane along with targeted portion of biological material is removed from the remaining layer of membrane and biological material. If bridges were formed, those bridges are mechanically broken upon lifting the carrier to free the adhered portions of targeted biological material. What remains is un-targeted biological material as shown in FIGS. 16 and 17. Being adhered to the membrane, the targeted biological material is removed with the carrier and available for further processing.

All publications and patent applications mentioned in this specification are incorporated herein by reference to the same extent as if each individual publication or patent application were specifically and individually indicated to be incorporated by reference.

The above description is illustrative and not restrictive. Many variations will be apparent to those skilled in the art upon review of this disclosure. The scope of the invention should not be determined with reference to the above description, but instead should be determined with reference to the appended claims and the full scope of their equivalents.

What is claimed is:

1. A method for laser microdissection comprising:
providing a first substrate having a surface;
applying a layer of biological material to the surface of the first substrate;
providing a second substrate having a surface with a transfer film disposed thereon, wherein the transfer film has adhesive characteristics upon activation by electromagnetic energy;

identifying at least one targeted portion of biological material to be microdissected, wherein the at least one targeted portion includes desired and undesired biological material;

bringing the transfer film into juxtaposition with the first substrate on the side of the biological material in the location of the at least one targeted portion of biological material;

activating a first laser source so as to describe at least one closed or substantially closed path around the at least one targeted portion of biological material to be microdissected, wherein the first laser source is configured to erode the biological material along the described path and defining an interior and exterior;

activating a second laser source and directing the second laser source at the interior of the at least one described path so as to activate at least one region of the transfer film so that the at least one activated region of transfer film adheres to the at least one interior portion of biological material, wherein the at least one activated region of transfer film adheres to at least one portion of the undesired biological material; and separating the second substrate with its attached transfer film and the at least one adhered targeted portion of biological material from the remaining layer of biological material.

2. The method of claim 1 wherein the first laser source is a UV laser source.

3. The method of claim 1 wherein the second laser source is an IR laser source.

4. The method of claim 1 wherein activating the first laser source includes describing a substantially closed path such that there remains at least one bridge between the interior to the exterior wherein the interior is joined to the surrounding exterior biological material at the at least one bridge.

5. The method of claim 4 wherein separating the second substrate with its attached transfer film and the at least one adhered targeted portion of biological material from the remaining layer of biological material includes breaking the at least one bridge.

6. The method of claim 4 wherein activating the second laser source includes activating the second laser source in between the location of the bridges.

7. The method of claim 1 wherein activating the second laser source includes activating the second laser source so as to describe at least one closed or partially closed curve at the interior of the at least one described path.

8. The method of claim 1 wherein activating the second laser source includes activating the second laser source more than one time in the interior of the at least one described path.

9. The method of claim 1 wherein bringing the second substrate with the transfer film into juxtaposition with the first substrate on the side of the biological material in the location of the at least one targeted portion of biological material includes contacting the transfer film to the biological material.

10. The method of claim 1 wherein bringing the second substrate with the transfer film into juxtaposition with the first substrate on the side of the biological material in the location of the at least one targeted portion of biological material includes spacing a substantial portion of the transfer film away from the biological material by a distance sufficient for promoting adhesion of the transfer film to the biological material upon activation of the transfer film by the second laser source.

\* \* \* \* \*